United States Patent [19]

Rubsamen et al.

[11] Patent Number: 5,558,085
[45] Date of Patent: Sep. 24, 1996

[54] INTRAPULMONARY DELIVERY OF PEPTIDE DRUGS

[75] Inventors: Reid M. Rubsamen, Berkeley; Lester J. Lloyd, Orinda, both of Calif.

[73] Assignee: Aradigm Corporation, Hayward, Calif.

[21] Appl. No.: 330,971

[22] Filed: Oct. 28, 1994

Related U.S. Application Data

[63] Continuation-in-part of Ser. No. 279,720, Jul. 25, 1994, Pat. No. 5,419,315, which is a continuation of Ser. No. 10,989, Jan. 29, 1993, abandoned.

[51] Int. Cl.⁶ ............................................. A61M 11/00
[52] U.S. Cl. ............................ 128/200.14; 128/204.23
[58] Field of Search ..................... 128/200.14, 200.23, 128/204.21, 204.23, 205.23

[56] References Cited

U.S. PATENT DOCUMENTS

| | | | |
|---|---|---|---|
| 3,812,854 | 5/1974 | Michaels et al. | 128/194 |
| 3,991,304 | 11/1976 | Hillsman | 235/151.34 |
| 4,106,503 | 8/1978 | Rosenthal et al. | 128/194 |
| 4,361,401 | 11/1982 | Smith Jr., et al. | 356/36 |
| 4,604,847 | 8/1986 | Moulding, Jr. et al. | 53/75 |
| 4,627,432 | 12/1986 | Newell et al. | 128/203.15 |
| 4,677,975 | 7/1987 | Edgar et al. | 128/200.14 |
| 4,686,231 | 8/1987 | Bender et al. | 514/333 |
| 4,819,629 | 4/1989 | Jonson | 128/203.22 |
| 4,877,989 | 10/1989 | Drews et al. | 310/323 |
| 4,926,852 | 5/1990 | Zoltan et al. | 128/200.23 |
| 4,934,358 | 6/1990 | Nilsson et al. | 128/200.23 |
| 4,984,158 | 1/1991 | Hillsman | 364/413.04 |
| 5,011,578 | 4/1991 | Wang et al. | 424/45 |
| 5,114,240 | 5/1992 | Kindt-Larsen et al. | 222/541.3 |
| 5,167,506 | 12/1992 | Kilis et al. | 434/262 |
| 5,363,842 | 11/1994 | Mishelevich et al. | 128/200.23 |

FOREIGN PATENT DOCUMENTS

| | | |
|---|---|---|
| 0186280 | 10/1985 | European Pat. Off. . |
| 0232235A2 | 8/1987 | European Pat. Off. . |
| 2104393 | 3/1983 | United Kingdom . |
| 2164269 | 3/1986 | United Kingdom . |
| 2255918 | 11/1992 | United Kingdom . |
| 2256805 | 12/1992 | United Kingdom . |
| WO87/05813 | 10/1987 | WIPO . |
| WO90/07333 | 7/1990 | WIPO . |
| WO91/14468 | 10/1991 | WIPO . |
| WO92/07599 | 5/1992 | WIPO . |
| WO92/07600 | 5/1992 | WIPO . |
| WO92/09322 | 6/1992 | WIPO . |
| WO92/15353 | 9/1992 | WIPO . |
| WO92/17231 | 10/1992 | WIPO . |
| WO93/17728 | 9/1993 | WIPO . |

OTHER PUBLICATIONS

Akjei, A. et al., "Pulmonary Delivery of Peptide Drugs: Effect of Particle Size on Bioavailability of the Leuprolide Acetate in Healthy Male Volunteers", Pharmaceutical Research, 1990, 7:565–567.

(List continued on next page.)

*Primary Examiner*—Aaron J. Lewis
*Attorney, Agent, or Firm*—Karl Bozicevic; Fish & Richardson P.C.

[57] ABSTRACT

A method of treating human patients is provided by the intrapulmonary delivery of a pharmaceutically active peptide formulation. The formulation is automatically released in an aerosolized form from a hand-held, self-contained, portable device comprised of a means for automatically releasing a measured amount of drug into the inspiratory flow path of a patient in response to information obtained from a means for measuring the inspiratory flow rate and determining the inspiratory volume of a patient. Reproducible dosing is obtained by providing for automatic release at the same inspiratory flow rate and inspiratory volume each time drug is released. The device includes a timer to enable a patient to take a drug at the same time each day. Further, overadministration of hormone formulations is avoided by providing a pre-programmed microprocessor designed to avoid overdosing.

31 Claims, 10 Drawing Sheets

OTHER PUBLICATIONS

Akjei, A. et al., "Bioavailability of Leuprolide following intratracheal administration to beagle dogs", 1990, International Journal of Pharmaceutics, 61:135–144.

Barrowcliffe, M. et al., "Pulmonary clearance of vasoactive intestinal peptide", 1986, Thorax 41:88–93.

Braquet, P., "Effect of endothelin–1 on blood pressure and bronchopulmonary system of the guinea pig", 1989, Journal of Cardiovascular Pharmacology, 13(Suppl. 5):S143–s146.

Camp, J., "Patient–controlled analgesia", 1991, AFP, 44:2145–2150.

Colthorpe, P. et al., "The Pharmacokinetics of Pulmonary––Delivered Insulin: A Comparison of Intratracheal and Aerosol Administration to the Rabbit", 1992, Pharmaceutical Research, 9:764–768.

Debs, R. et al., "Lung–specific delivery of cytokines induces sustained pulmonary and systemic immunodulation in rats", 1988, Journal of Immunology, 140:3482–3488.

Gourlay, G. K., et al. "Fentanyl Blood Concentration–Analgesic Response Relationship in the Treatment of Postoperative Pain", 1988, Anesth. 67:329–337.

Harrison, T. R. et al., "Harrison's Principles of Internal Medicine" (10th edition), 1983, pp. 666–674.

Hubbard, R. C. et al., "Anti–Neutrophil–Elastase Defenses of the Lower Respiratory Tract in a1–Antitrypsin Deficiency Directly Augmented with an Aerosol of a1–Antitrypsin", Annals of Internal Medicine, 111:206–212.

Hubbard, R. C. et al., "Fate of aerosolized recombinant DNA–produced a1–antitrypsin:Use of the epithelial surface of the Lower respiratory tract to administer proteins of therapeutic importance", 1989, Proc. Natl. Acad. Sci. USA 86:680–694.

Jaffe, A. B., et al., "Rats self–administer Sufentanil in Aerosol Form", 1989, Psychopharmacology, 99:289–293.

Kohler, D., "Aerols for Systemic Treatment", 1990, Lung, Suppl.:677–684.

Laube, Beth L. et al., "Aerosolized Insulin Delivered Through The Lungs Is Effective In Normalizing Plasma Glucose Levels In Non–Insulin Dependent Diabetic Subjects", 1991, J. Aerosol Medicine, 4:286.

Laube, Beth L., "Preliminary Study of the Efficient of Insulin Aerosol Delivered by Oral Inhalation in Diabetic Patients", 1993, JAMA 269:2106–2109.

Lee, V. H., "Changing Needs in Drug Delivery in the Era of Peptide and Protein Drugs", Marcel Dekker, N. Y., pp. 1–11.

Lehman, K. A. et al., 1991, "Transdermal Fentanyl for the Treatment of Pain After Major Urological Operations", Eur. J. Clin. Phamacol. 41:17–21.

Mather, L. E., "Pharmacokinetics and Patient–Controlled Analgesia(*)", 1992, Acta Anaesthesiologica Belgica, 43:5–20.

Miller, R., "Anesthesia Second Edition", 1986, Churchill Livingstone, 1:762.

Moses et al., "Insulin Administered Intranasally as an Insulin–Bile Salt Aerosol—Effectiveness and Reproducibility in Normal and Diabetic Subjects", 1983, Diabetes 32:1040–1047.

Newman, S. P. et al., "How should a pressurized β–adrenergic bronchodilator be inhaled?", 1981, Eur. J. Respir. Dis. 62:3–21.

Newman, S. P. et al., "Deposition of pressurized suspension aerosols inhaled through extension devices", 1981, Am. Rev. Respir. Dis. 124:317–320.

Newman, S. P. et al., "Deposition of Pressurized Aerosols in the Human Respitory Tract", 1981, Thorax, 36:52–55.

Newman, S. P., "Deposition and Effects of Inhalation Aerosols", 1983, Dept. of Thoracic Medicine.

Nieminen et al., "Aerosol Deposition in Automatic Dosimeter Nebulization" 1987, European Journal of Respiratory Diseases, 71:145–152.

Patton, J. S. et al., "Routes of Delivery: Case Studies—Pulmonary delivery of peptides and proteins for systemic action", 1992, Advanced Drug Delivery Reviews, 8:179–196.

Rapp, R. P. et al., "Patient–controlled analgesia:a review of effectiveness of therapy and an evaluation of currently available devices", 1989, DICP, The Annals of Pharmacotherapy 23:899–904.

Rosenberg, M., "Patient–Controlled Analgesia", 1992, J. Oral Maxillofac. Surg. 50:386–389.

Rowbotham, D. J., "A disposable device for patient–controlled analgesia with fentanyl", 1989, Anaesthesia, 44:922–924.

Ryder, E., "The history of patient–controlled analgesia", 1991, Journal of Intravenous Nursing, 14(6):372–381.

Salzman, R., et al., "Intranasal Aerozolized Insulin Mixed––Meal Studies and Long–Term Use in Type I Diabetes", 1985, New England Journal of Medicine, 213:1078–1084.

Shade, P., "Patient–controlled Analgesia: Can Client Education Improve Outcomes?", 1992, Journal of Advanced Nursing, 17:408–413.

Smith, Robert M., et al., "Pulmonary Deposition and Clearance of Aerosolized Alpha–1–Proteinase Inhibitor Administered to Dogs and to Sheep", 1989, J. Clin. Invest. 84:1145–1154.

Smythe, M., "Patient–controlled Analgesia:A Review", 1992, Pharmacotherapy, 99:289–293.

Wearley, Lorraine L., "Recent Progress in Protein and Peptide Delivery by Noninvasive Routes", 1991, Critical Reviews in Therapeutic Drug Systems, 8:331–392.

Wigley, F. M. et al., "Insulin Across Respiratory Mucosae by Aerosol Delivery" 1971, Diabetes, 20:552–556.

"Recent Progress in Protein and Peptide Delivery by Noninvasive Routes", by Lorraine L. Wearley; Critical Reviews in Therapeutic Drug Carrier Systems, 8(4):331–394 (1991).

"How Should A Pressurized Badrenergic Bronchodilator Be Inhaled?", by Stephen P. Newman et al.; Eur. J. Respir. Dis. (1981) 62, 3–721.

INTRAPULMONARY DELIVERY OF PEPTIDE DRUGS

CROSS REFERENCE TO RELATED APPLICATIONS

This application is a continuation-in-part of earlier filed application Ser. No. 08/279,720 filed Jul. 25, 1994, now U.S. Pat. No. 5,419,315, which is a file-wrapper-continuation application of application Ser. No. 08/010,989 filed Jan. 29, 1993 now abandoned, which applications are incorporated herein by reference and to which applications is claimed priority under 35 USC § 120.

FIELD OF THE INVENTION

This invention relates generally to methods of administering peptides for endocrine therapy. More specifically, this invention relates to the intrapulmonary delivery of peptide hormone drugs from a hand-held, self-contained device which automatically and repeatedly releases a controlled amount of peptide drug to a patient at the same point in the respiratory cycle of the patient based on both inspiratory flow rate and inspiratory volume so as to obtain a high degree of repeatability in dosing.

BACKGROUND OF THE INVENTION

Potent peptide hormones are available for a variety of therapeutic indications. Leuprolide, for example, is a GnRH super-agonist useful in the treatment of endometriosis and prostrate cancer. Leuprolide also has potential applications in the field of breast cancer management and the treatment of precocious puberty. Calcitonin enhances metabolism and may be a useful therapeutic agent for the management of osteoporosis, a common complication of aging.

To treat conditions or diseases of the endocrine system, pharmaceutical formulations containing potent peptide hormones are typically administered by injection. Because the stomach presents a highly acidic environment, oral preparations of peptides are unstable and readily hydrolyzed in the gastric environment. Currently, there are no oral preparations of therapeutic peptide agents available.

Both calcitonin and leuprolide can be administered nasally. (See Rizzato et al., *Curr. Ther. Res.* 45:761–766, 1989.) Both drugs achieve blood levels when introduced into the nose from an aerosol spray device. However, experiments by Adjei et al. have shown that the bioavailability of leuprolide when administered intranasally is relatively low. Adjei and Garren, *Pharmaceutical Research*, Vol. 7, No. 6, 1990.

An increase in the bioavailability of leuprolide can be obtained by administering the drug into the lung. Intrapulmonary administration of leuprolide has been shown to be an effective means of non-invasive administration of this drug. Adjei and Garren, *Pharmaceutical Research*, Vol. 7, No. 6, 1990. Intrapulmonary administration of leuprolide and other peptide drugs has the additional advantage of utilizing the large surface area available for drug absorption presented by lung tissue. This large surface area means that a relatively small amount of drug comes into contact with each square centimeter of lung parenchyma. This fact reduces the potential for tissue irritation by the drug and drug formulation. Local irritation has been seen with nasal delivery of insulin and has been a problem for commercialization of nasal preparations of that drug.

It is a problem with peptide hormones that they are very potent with effects that are not immediately manifested. For example, therapy with leuprolide for prostrate cancer does not typically produce any acute clinical effects. Similarly, prophylaxis against osteoporosis with calcitonin will not produce any acute symptoms discernible to the patient. Therefore, administration of each dose of these drugs must be reliable and reproducible. In addition, careful compliance monitoring is important to avoid therapeutic failures by carefully following the patient's adherence to the prescribed dosing regiment.

In addition, because these drugs are potent therapeutic agents, care must be taken to avoid overdosing.

The most convenient form for intrapulmonary administration of drugs by ambulatory patients is through the use of a metered dose inhaler. Metered dose inhaler devices allow the self-administration of a metered bolus of drug when the device is manually actuated by the patient during inspiration. However, such devices must be used with the proper inspiratory maneuver in order to promote effective deposition of the drug into the lung. In addition to performing a correct inspiratory maneuver, the patient must self-actuate the metered dose inhaler during the appropriate part of the inspiratory cycle. Further, when using such devices, it is not typically self-evident to the patient that the drug was properly or improperly administered. For those drugs without immediate clinical effect, the patient can easily misuse the metered dose inhaler and be under the false impression that he is correctly self-administering the drug as prescribed. Similarly, the patient may be under the false impression that he performed an incorrect inspiratory maneuver in metered dose inhaler actuation when he in fact properly performed these operations and received an appropriate amount of drug.

Devices exist to deliver metered dose inhaler drugs into the lung in a breath-actuated manner. However, such devices do not measure inspiratory flow rate and determine inspiratory volume in order to trigger the device. Therefore, a sub-optimal inspiratory maneuver (e.g. one with too high of an inspiratory rate) could be used to actuate the device and produce a sub-optimal deposition pattern of drug into the lungs resulting in a sub-therapeutic blood level of the therapeutic agent being delivered. If delivery took place at the correct point in the inspiratory cycle the dose delivered would be high—overall dosing would be erratic in that drug is released at different points in the inspiratory cycle.

When using a metered dose inhaler, the dosing events must be manually recorded by the patient. Many potent therapeutic hormone peptide drugs are given only once a day. It is important that the patient remember to take the prescribed daily dose, and that the dose be taken at the correct time of the day. Further, it is important that the patient not take more than the prescribed number of doses per day. The timing of delivery of potent therapeutic hormone peptide drugs is critical because these drugs interact intimately with the chronobiology of the patient's physiology in order to produce their desired effect.

When using standard metered dose inhaler devices, the patient must manually record the time of each dosing administration. In addition, the patient must remember when to self-administer the drug. Devices exist for recording automatically metered dose inhaler drug delivery events. However, such devices do not record the presence of inspiratory flow at the time of device firing. This means that a noncompliant patient can fire the metered dose inhaler into the air and have a valid drug dosing event recorded on the self-containing recording means. In addition, the patient could self-administer the drug with an inappropriate inspiratory maneuver and have a valid drug dosing event recorded by the device. This would lead the physician to assume that the patient was compliant when he was receiving an inappropriate amount of drug with each dosing event.

SUMMARY OF THE INVENTION

A method of treating human patients is provided by the intrapulmonary delivery of a pharmaceutically active peptide formulation. The formulation is automatically released in an aerosolized form from a hand-held, self-contained, portable device comprised of a means for automatically releasing a measured amount of drug into the inspiratory flow path of a patient in response to information obtained from a means for measuring the inspiratory flow rate and determining the inspiratory volume of a patient. Reproducible dosing is obtained by providing for automatic release at the same inspiratory flow rate and inspiratory volume (determined in real time) each time drug is released. The methodology involves measuring for, determining and/or calculating a firing point or drug release decision based on instantaneously (or real time) calculated, measured and/or determined inspiratory flow rate and inspiratory volume points. The device includes a timer to enable a patient to take a drug at the same time each day. Further, overadministration of hormone formulations is avoided by providing a pre-programmed microprocessor designed to avoid overdosing.

It is an object of this invention to describe a method of aerosolized delivery of pharmaceutically active peptide drugs in a safe and effective manner.

An advantage of the present invention is that it can be used for ambulatory patients.

It is a feature of the invention that the device used for the aerosolized delivery of hormone formulations records the time and amount of formulation delivered.

Another advantage of the present invention is that the device used for delivering hormone formulations includes a timer which emits an audible and/or visual signal to the patient at each scheduled dosing event.

Yet another advantage of the present invention is that the method involves administering hormone formulations while simultaneously keeping an index which corresponds to the quality of the patient's inspiratory flow profile at each dosing event.

Another feature of the present invention is that when carrying out the method of delivery, a record of the date and time of each dosing event is electronically and automatically produced within a unitary device which delivers the drug.

Another advantage of the present invention is that the device presents a visual display calendar which calendar specifically indicates to the patient the day and/or time a dose was administered.

Another feature of the present invention is that the device for administering drug includes a microprocessor programmed to prevent the administration of more doses than are prescribed for the particular deficiency being treated.

Another advantage of the present invention is that better treatment protocols can be developed by the treating physician by transferring information from the delivery/recording device to a printout device which can be reviewed in order to determine the complete compliance history of the patient.

Another object of this invention is to provide an apparatus which can analyze the breathing pattern of the patient and can measure the respiratory flow rate and measure the inspiratory volume at the same time in order to determine the optimal point in the inspiratory cycle for delivery of aerosolized peptide drugs.

Another advantage is that the method described provides for reproducible delivery of peptide hormones such as leuprolide wherein the reproducibility is a critical part of treatment causing each dose of hormone to have the same clinical effect.

Another object is to provide a method of providing endocrine therapy to ambulatory patients wherein an aerosolized formulation of a peptide drug is repeatedly delivered to the patient at the same inspiratory volume (in the range of 0.15 to 0.8 liters) and the same inspiratory flow rate (in the range of 0.1 to 2.0 liters per sec).

Another feature of this invention is that formulations of peptide drugs such as leuprolide in a highly volatile propellant provide for a fundamentally tamper-resistant package.

It is another object of the invention to provide a metered-dose inhaler canister comprising a formulation of a peptide drug such as leuprolide packaged in a manner such that it will remain stable and active for long storage times.

A feature of the invention is that it can monitor the amount of aerosolized peptide drug delivered to a patient and record amounts and times of delivery for review by a treating physician.

These and other objects, advantages and features of the present invention will become apparent to those skilled in the art upon reading this disclosure in combination with drawings wherein like numerals refer to like components throughout.

BRIEF DESCRIPTION OF THE DRAWINGS

FIG. 1 is a cross-sectional plan view of a drug delivery device;

FIG. 2 is a cross-sectional plan view of a more preferred embodiment of a drug delivery device;

FIG. 3 is a perspective view showing a pressurized canister with the canister cover components disconnected;

FIG. 4 is a perspective view of another embodiment of the cover components connected and the canister held therein;

FIG. 5 is a graph showing data points plotted in four general areas with the points plotted relative to inspiratory flow rate (on the abscissa) and inspiratory volume (on the ordinate) in two dimensions;

FIG. 6 is a graph showing the four general areas plotted per FIG. 1 now plotted with a third dimension to show the percentage of drug reaching the lungs based on a constant amount of drug released;

FIG. 7 is a three dimensional graph showing the therapeutic values for inspiratory flow rate and inspiratory volume which provide better drug delivery efficiency;

FIG. 8 shows a preferred range of the valves shown in FIG. 7;

FIG. 9 shown a particularly preferred range for the valves of FIG. 7; and FIG. 10 is a schematic view of an embodiment of a drug delivery device which can be used with the method of the invention; and FIG. 11 is a schematic view of a peptide drug containing package.

DETAILED DESCRIPTION OF THE PREFERRED EMBODIMENTS

Figure 1:
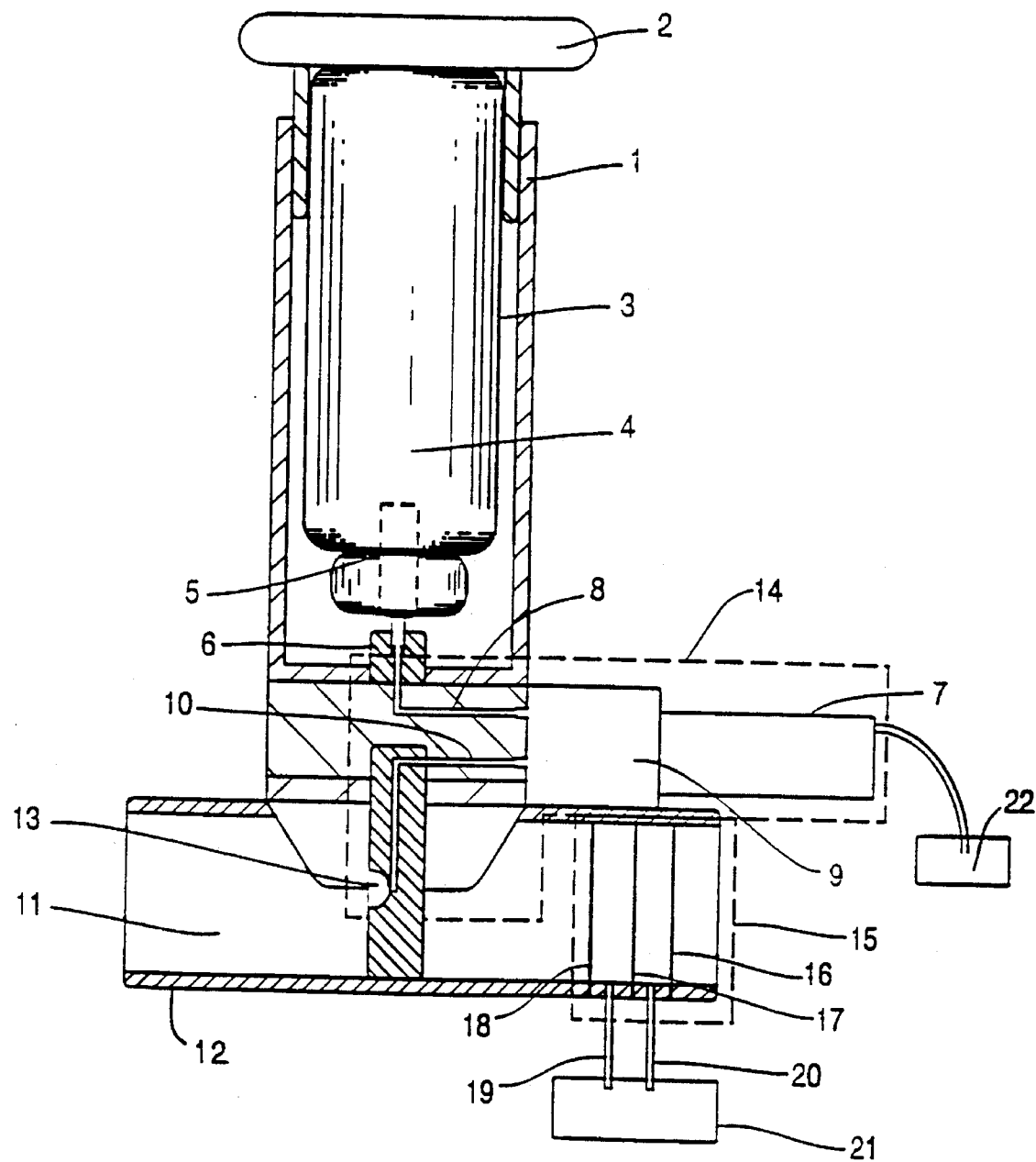

Before the present method of endocrine therapy and devices, packages and formulations used in connection with such are described, it is to be understood that this invention is not limited to the particular methodology, devices, packages and formulations described, as such methods, devices, packages and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an aerosolized compound" includes a plurality of such compounds, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The terms "hormone," "hormone drug," "pharmaceutically active hormone formulation," "peptide used in endocrine therapy," "peptide hormone drug," "peptide drug" and the like are used interchangeably herein. A hormone drug as described herein is a peptide drug which has been prepared in a pharmaceutically effective formulation and is useful in endocrine therapy. Specifically, a peptide drug of the type described herein is useful for exogenously modifying the behavior of a patient's endocrine system. Drugs which are used in the present invention include those listed in Table 1, it being noted that these peptides preferably contain less than 50, more preferably less than 27, amino acids. Drug of smaller size are preferred. Particularly useful drugs for use with the invention include leuprolide and calcitonin, and nafarelin.

The term "dosing event" shall be interpreted to mean the administration of peptide drug to a patient in need thereof by the intrapulmonary route of administration which event may encompass one or more releases of drug formulation from a drug dispensing device over a period of time of 15 minutes or less, preferably 10 minutes or less, and more preferably 5 minutes or less, during which period multiple inhalations are made by the patient and multiple doses of peptide drug are released and inhaled. A dosing event shall involve the administration of peptide drug to the patient in an amount of about 1 μg to about 10 mg in a single dosing event which may involve the release of from about 10 μg to about 100 mg of peptide drug from the device.

The term "velocity of the drug" shall mean the average speed of particles moving from a drug release point such as a valve to a patient's mouth.

The term "measuring" describes an event whereby both the inspiratory flow rate and inspiratory volume of the patient is determined, measured and/or calculated in order to determine an optimal point in the inspiratory cycle at which to release aerosolized peptide drug formulation. It is also preferable to continue measuring inspiratory flow during and after any drug delivery and to record inspiratory flow rate and volume before, during and after the release of drug. Such reading makes it possible to determine if peptide drug formulation was properly delivered to the patient. A microprocessor or other device can calculate volume based on a measured flow rate. When either flow rate or volume becomes known in any manner it can be said to have been determined.

The term "monitoring" event shall mean measuring lung functions such as inspiratory flow rate, and/or inspiratory volume so that a patient's lung function as defined herein, can be evaluated before and/or after drug delivery thereby making it possible to evaluate the effect, if any, of peptide drug delivery on the patient's lung function.

The term "inspiratory flow rate" shall mean a value of air flow measured, calculated and/or determined based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a measured, calculated and/or determined volume of air passing a given point into the lungs of a patient assuming atmospheric pressure ±5% and a temperature in the range of 10° C. to 40° C.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. The point within the inspiratory cycle where drug is released may be based on a point within the inspiratory cycle likely to result in the maximum delivery of drug and based and/or on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The terms "formulation" and "liquid formulation" and the like are used interchangeably herein to describe any pharmaceutically active drug by itself or with a pharmaceutically acceptable carrier in flowable liquid form and preferably having a viscosity of not more than 25% greater than the viscosity of water. Such formulations are preferably solutions, e.g. aqueous solutions, ethanolic solutions, aqueous/ethanolic solutions, saline solutions and colloidal suspensions. Formulations can be solutions or suspensions of drug in a low boiling point propellant.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

General Methodology

A non-invasive means of endocrine therapy is provided in a manner which makes it possible to maintain tight control over the amount of drug administered to a patient and precise timing in terms of when the drug is administered. An essential feature of the invention is the intrapulmonary delivery of a peptide drug to the patient in a controlled and repeatable manner. The device of the invention provides a number of features which make it possible to achieve the controlled and repeatable dosing procedure required for successful endocrine therapy. Specifically, the device is not directly actuated by the patient in the sense that no button is pushed nor valve released by the patient applying physical pressure. On the contrary, the device of the invention provides that the valve which releases hormone drug is opened automatically upon receipt of a signal from a microprocessor programmed to send a signal when data is received from a monitoring device such as an airflow rate monitoring device.

Delivery devices used to carry out the present invention record specific information relating to both monitoring events and dosing events and can be programmed to react to various changes in order to optimize patient treatment. Specifically, the device includes an ability to record monitoring events in order to develop an inspiratory flow profile of the patient which makes it possible to provide for greater repeatability with respect to dosing. Further, the device specifically records the time and amount of hormone drug released at each dosing event. The day and time of day of drug release is recorded. The device is equipped with a visual and audio signaling means which tell the patient when and/or how much peptide drug to take. The audio means is programmed so as to send an audio signal when the patient is to begin a monitoring event to be followed by a dosing event. The visual display indicates specific information such as providing instructions to the patient including "conduct monitoring event" and "proceed with dosing event." Further, the visual display will indicate a calendar of days and specifically indicate on the calendar when dosing took place on the given day. Accordingly, the patient can quickly determine by visual examination whether hormone drug was delivered on any given day. It is important to administer peptide hormone drugs at the same time each day as natural hormone release (and thus hormone administration) is closely connected to the chronobiology of the patient.

A patient using the device withdraws air from a mouthpiece and the inspiratory rate, and calculated inspiratory volume of the patient are measured one or more times in a monitoring event which determines a preferred point in an inhalation cycle for the release of a dose of peptide drug. Inspiratory flow is measured and recorded in one or more monitoring events for a given patient in order to develop an inspiratory flow profile for the patient. The recorded information is analyzed by the microprocessor in order to deduce a preferred point within the patient's inspiratory cycle for the release of peptide drug with the preferred point being calculated based on the most likely point to result in a reproducible delivery event.

It is pointed out that the device of the present invention can be used to, and actually does, improve the efficiency of drug delivery. However, this is a secondary feature. The primary feature is the reproducibility of the release of a tightly controlled amount of drug at a particular point in the respiratory cycle so as to assure the delivery of a controlled and repeatable amount of drug to the lungs of each individual patient.

The combination of automatic control of the valve release, combined with frequent monitoring events in order to calculate the optimal flow rate and time for the release of peptide drug, combine to provide a repeatable means of delivering peptide drug to a patient. Because the valve is released automatically and not manually, it can be predictably and repeatedly opened for the same amount of time each time or for the preprogrammed measured amount of time which is desired at that particular dosing event. Because dosing events are preferably preceded by monitoring events, the amount of peptide drug released and/or the point in the inspiratory cycle of the release can be readjusted based on the particular condition of the patient. For example, if the patient is suffering from a condition which allows for a certain degree of pulmonary insufficiency, such will be taken into account in the monitoring event by the microprocessor which will readjust the amount and/or point of release of the peptide drug in a manner calculated to provide for the administration of the same amount of peptide drug to the patient at each dosing event.

Figure 5:
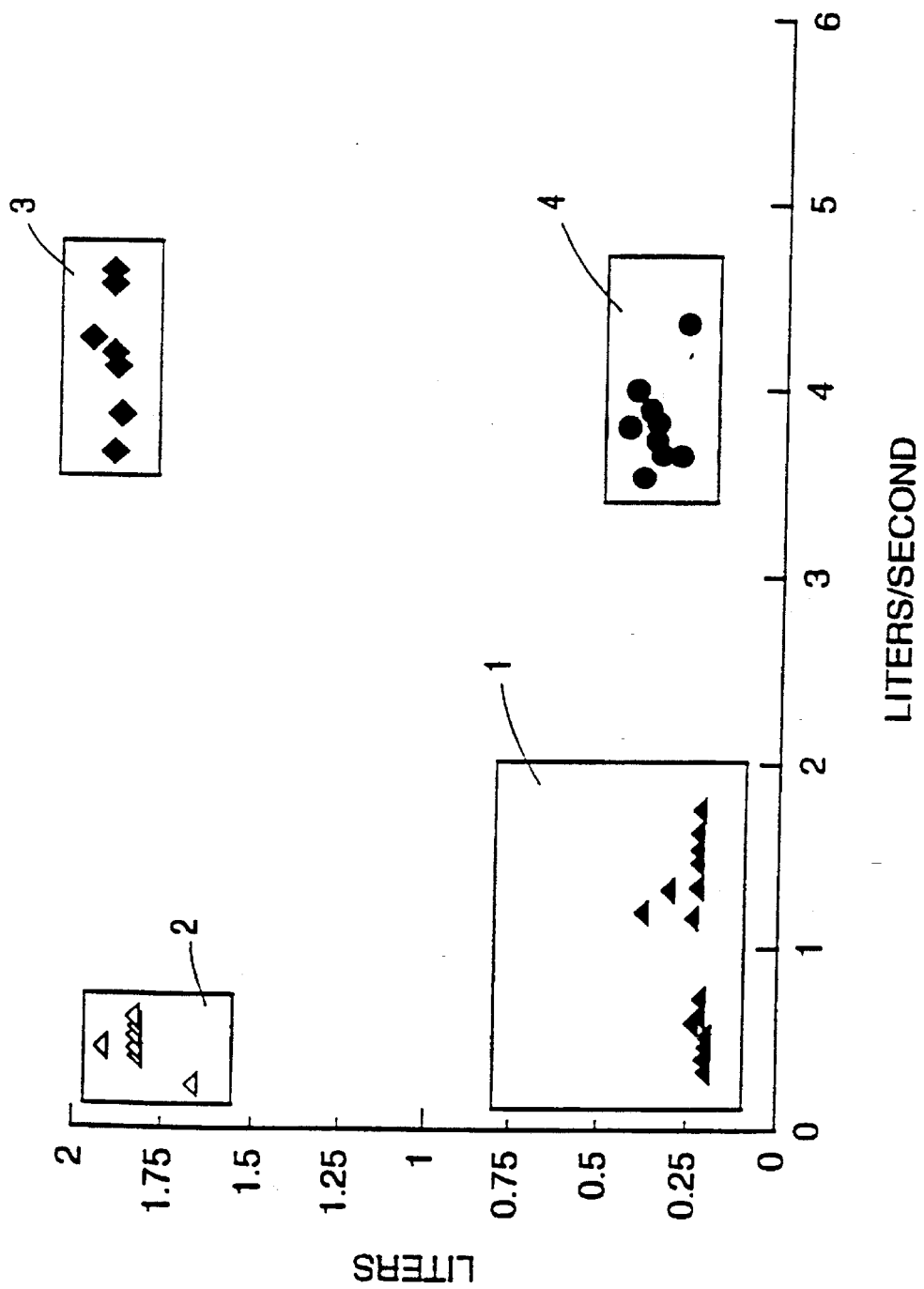

FIG. 5 is a two-dimensional graph wherein the inspiratory flow rate is plotted against the inspiratory volume. The patient's inspiratory flow rate and inspiratory volume are simultaneously and separately measured. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 5 the microprocessor was programmed to release drug in four general areas with respect to the inspiratory flow rate and inspiratory volume parameters. This resulted in data points being plotted in four general areas on the two-dimensional graph of FIG. 5. The four areas are labeled 1, 2, 3 and 4. In area 1 (showing solid triangles), the drug was released when the patient's inspiratory flow rate was "slow to medium" (0.10 to 2.0 liters per sec) with an "early" inspiratory volume of 0.15 to 0.8 liters. In area 2 (showing open triangles), the drug was released at a "slow" inspiratory rate/0.10 to 1.0 liters/sec) and a "late" volume (1.6 to 2.8 liters). In area 3 (showing solid diamonds), the drug was released at a "fast" inspiratory flow rate (3.5 to 4.5 liters/sec) and a "late" volume. In area 4 (showing solid circles), the drug was released at a fast inspiratory flow rate and an "early" inspiratory volume.

The results shown in FIG. 5 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously and separately consider (in real time) both inspiratory flow rate and inspiratory volume when determining the point for drug release for intrapulmonary drug delivery. Changes in either parameter can greatly effect the amount of drug deposited. Thus, when treating a patient the drug should be released at approximately (±10%, preferably ±5% and most preferable as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined to precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 6.

Figure 6:
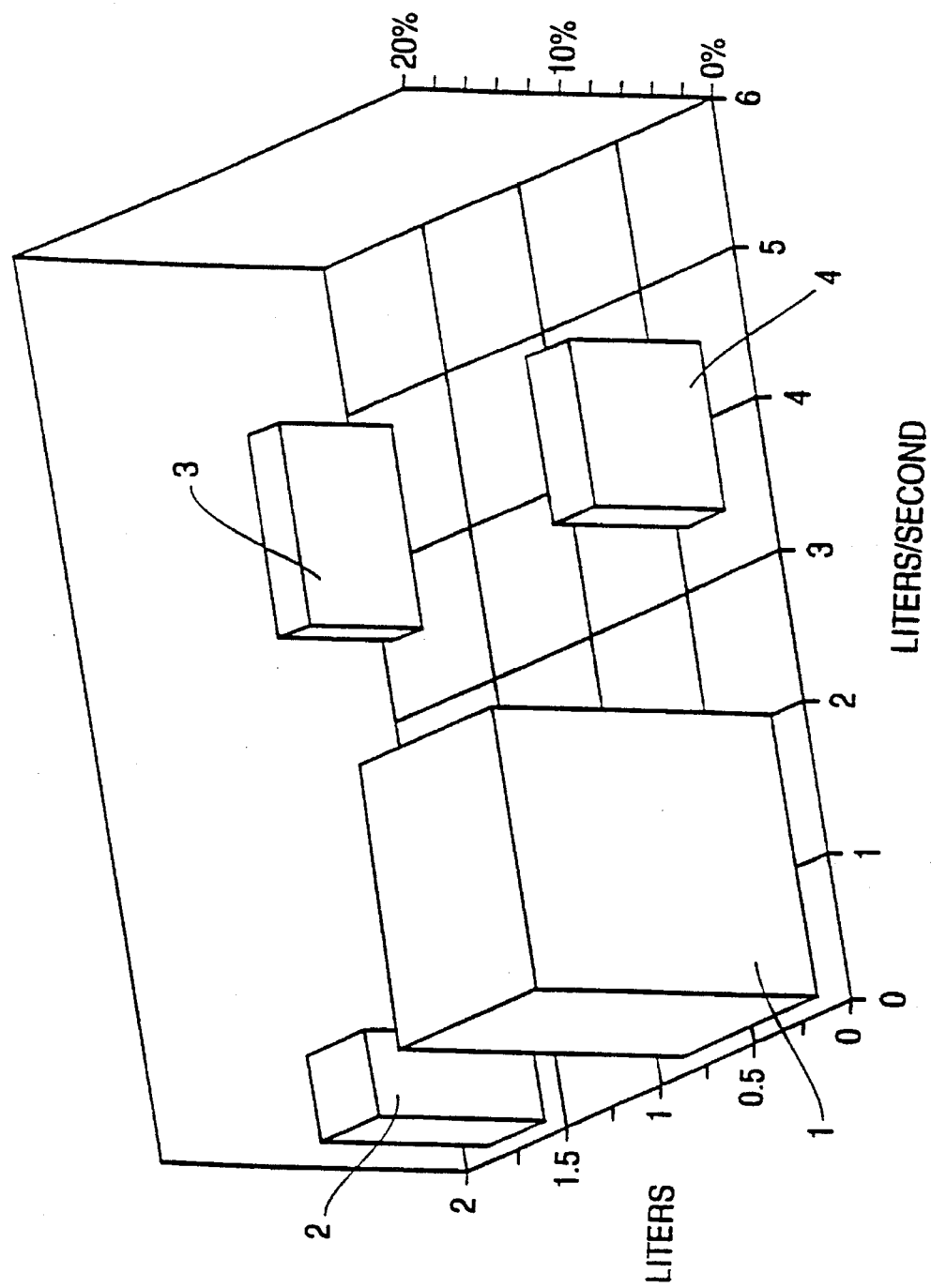

The third dimension as shown in FIG. 6 (the height of the four columns) indicates the percentage amount of drug deposited based on the total amount of drug released to the patient. The area labeled 1 clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within an inspiratory flow rate range of 0.10 to 2.0 liters per second and at an inspiratory volume in the range of about 0.15 to about 0.80 liters. This range is shown by the rectangularly shaped column of FIG. 7.

In that intrapulmonary drug delivery systems often provide for erratic dosing it is important to provide a method which allows for consistent, repeatable dosing. This is obtained by simultaneously and separately considering both inspiratory flow rate and inspiratory volume in order to determine a point by its abscissa and ordinate. If both measurements are separately considered the drug can be released anywhere along the abscissa and ordinate scales shown in FIG. 5. Once a point is selected (such as by randomly selecting a point in box 1 of the graph of FIG. 5) that selected point (with the same coordinates) is used again and again by a given patient to obtain repeatable dosing. If only one parameter is measured (abscissa or ordinate) and drug is released based on that parameter the drug release point is defined by a line on the graph of FIG. 5. When drug is released again the release can be at any point on that line. For example, the inspiratory flow rate (measured horizontally on the abscissa) might be defined by a point. However, the inspiratory volume (which was not measured and/or considered) would be defined only by a vertical line. Thus, subsequent releases would be at different volumes along that vertical line and the dosing would not be consistent. By measuring both inspiratory flow rate on the abscissa and inspiratory volume on the ordinant the coordinates will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box 1 of FIG. 5.

Figure 7:
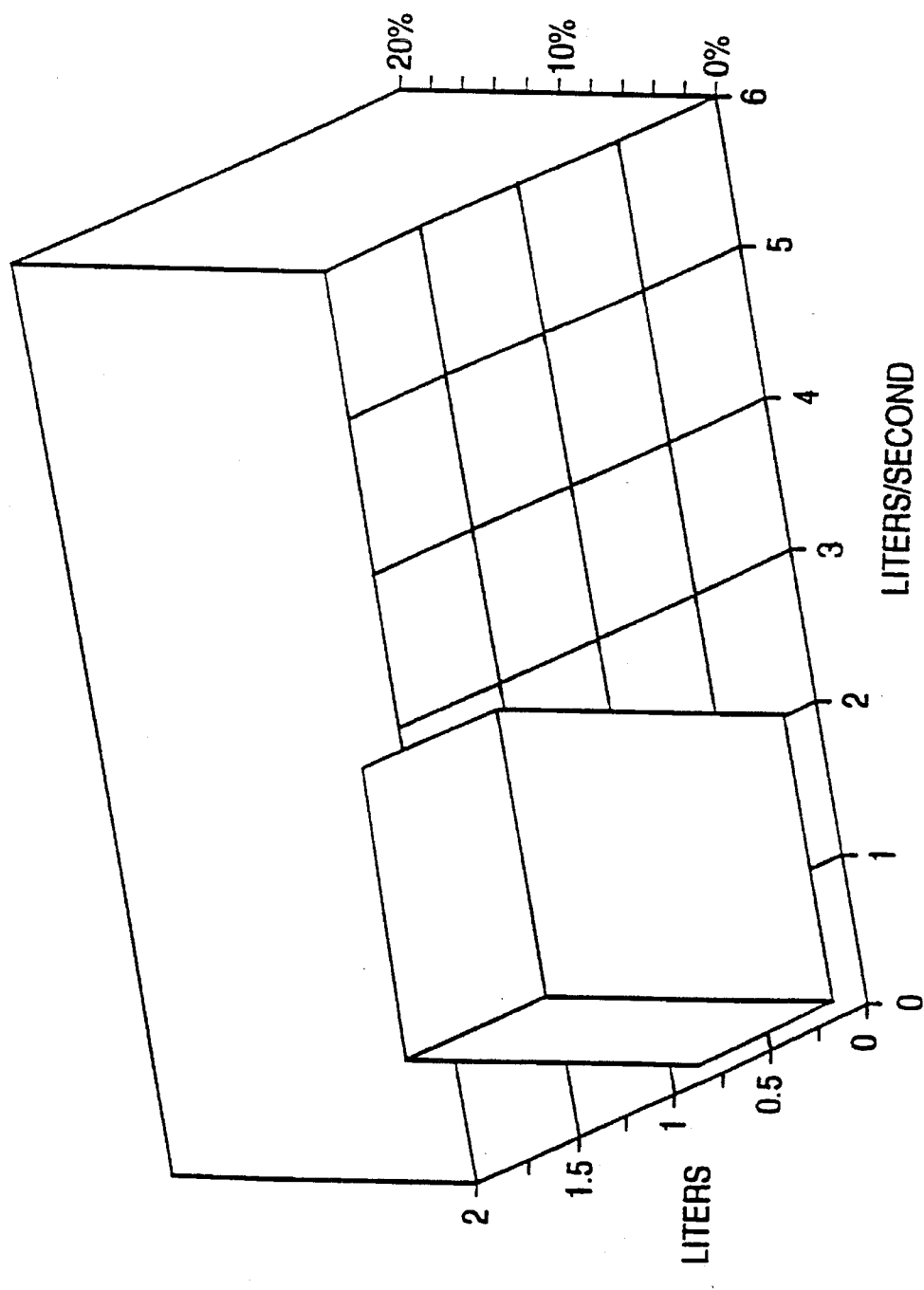
Figure 8:
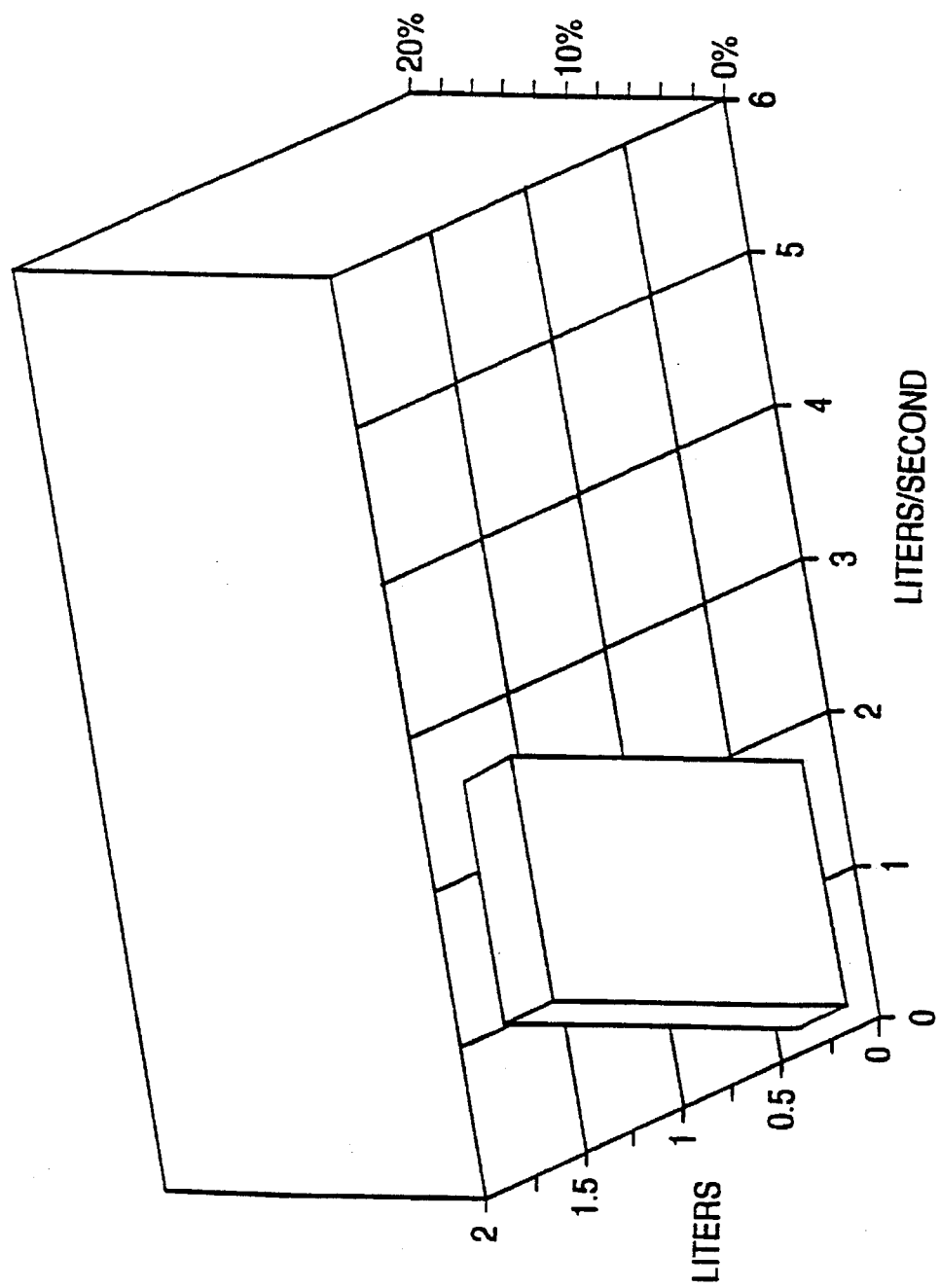
Figure 9:
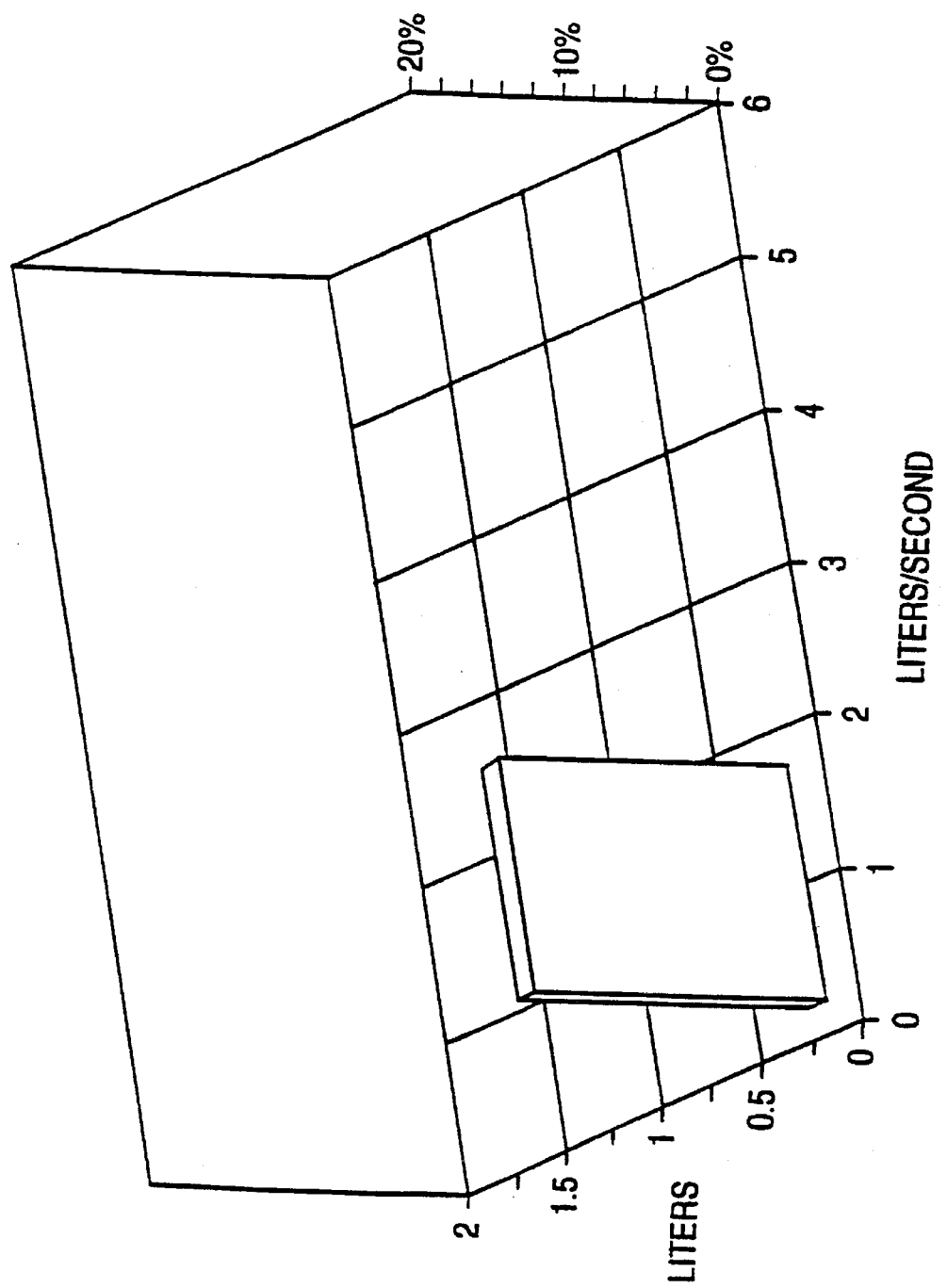

By examining delivery of drug associated with the data points plotted in FIG. 5, it is possible to determine a preferred and particularly preferred and most preferred range as per FIGS. 7, 8 and 9. The preferred range of FIG. 7 shows drug released at a volume of 0.15 to 0.8 liters and rate of 0.10 to 2.0 liters/second. The particularly preferred range plotted in FIG. 8 indicates that the inspiratory flow should be within the range of 0.2 to about 1.8 liters per second with an inspiratory volume in the range of 0.15 to about 0.4 liters. The most preferred range (FIG. 9) is from about 0.15 to about 1.8 liters per second for the inspiratory flow rate and about 0.15 to about 0.25 liters for the inspiratory volume. Thus, preferred delivery can be obtained by (1) repeatedly delivering aerosolized formulation to a patient at the same simultaneously and separately measured inspiratory flow rate and inspiratory volume and (2) releasing drug to the patient within specified therapeutically effective ranges as shown within FIGS. 7, 8 and 9. The invention involves releasing drug (after measuring) inside the ranges as per FIGS. 7, 8 or 9. Thus; the release could begin inside or outside the range. Preferably the drug release begins inside the range and more preferable begins and ends inside the ranges of FIGS. 7, 8 or 9.

The methodology of the invention may be carried out using a portable, hand-held, battery-powered device. As per U.S. Patent application Ser. No. 08/002,507 filed Jan. 29, 1993 incorporated herein by reference. In accordance with another system the methodology of the invention could be carried out using the device, dosage units and system disclosed in U.S. Patent application Ser. No. 08/247,012 filed May 20, 1994. In accordance with the system the drug is included in an aqueous formulation which is aerosolized by moving the formulation through a porous membrane. Alternatively, the methodology of the invention could be carried out using a mechanical (non-electronic) device. Those skilled in the art recognized that various components can be mechanically set to actuate at a given inspiratory flow rate (e.g. a spring biased valve) and at a given volume (e.g. a spinable flywheel which rotates a given amount per a given volume). The components of such devices could be set to allow drug release inside the parameters of FIGS. 3, 4 or 5.

The drug which is released to the patient may be in a variety of different forms. For example, the drug may be an aqueous solution of drug, i.e., drug dissolved in water and formed into small particles to create an aerosol which is delivered to the patient. Alternatively, the drug may be in a solution wherein a low-boiling point propellant is used as a solvent.

Some peptide drugs are subject to being degraded more quickly when in solution such as an aqueous solution. Preferably such drug are packaged in a dry form and mixed with water prior to administration. Alternately, the drug is kept in the form of a dry powder which is intermixed with an airflow in order to provide for particlized delivery of drug to the patient.

Regardless of the type of drug or the form of the drug formulation, it is preferable to create drug particles having a size in the range of about 0.5 to 5 microns. By creating drug particles which have a relatively narrow range of size, it is possible to further increase the efficiency of the drug delivery system and improve the repeatability of the dosing. Thus, it is preferable that the particles not only have a size in the range of 0.5 to 5 microns but that the mean particle size be within a narrow range so that 80% or more of the particles being delivered to a patient have a particle diameter which is within ±50% of the average particle size, preferably ±20% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. Accordingly, the drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero. The velocity may be slightly negative, i.e., in a direction away from the patient. The velocity may range from −2.0 liters/sec to 2.0 liters/sec and is preferably zero. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

An aerosol may be created by forcing drug through pores of a membrane which pores have a size in the range of about 0.25 to 2.5 microns. When the pores have this size the particles which escape through the pores to create the aerosol will have a diameter in the range of 0.5 to 5 microns. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 0.5 to 5 microns.

The drug formulation may be a low viscosity liquid formulation (a viscosity within 25% plus or minus of water). The viscosity of the drug by itself or in combination with a carrier must be sufficiently low so that the formulation can be forced out of openings to form an aerosol, e.g., using 20 to 200 psi to form an aerosol preferably having a particle size in the range of about 0.5 to 5 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration.

The amount of peptide drug delivered to the patient will vary greatly depending on the particular drug being delivered. In accordance with the present invention it is possible to deliver a wide range of peptide drugs. For example, drugs included within the container could be drugs which have a systemic effect e.g. leuprolide or a local effect in the lungs e.g. Activase.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug using the proper techniques and still not obtained the correct results a different drug or dosing methodology might be recommended.

The method of endocrine therapy may be carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow, rate and volume of a patient, and (d) a switch for automatically releasing or firing the mechanical means after the inspiratory flow and/or volume reaches a threshold level. The device may also include a transport mechanism to move the package from one container to the next. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure or vibration) to move drug from a container on the package into the inspiratory flow path of the device and ultimately into the patient's lungs. After being released, the drug and carrier will pass through a porous membrane which is vibrated to aerosolize the formulation and thereafter the lungs of the patient. Containers and systems of the type described above are disclosed and described in U.S. patent application Ser. No. 08/247,012 filed May 20, 1994 which is incorporated herein by reference to disclose and describe such containers and systems.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

The details of a drug delivery device which includes a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and it is specifically incorporated in order to describe and disclose the microprocessor and program technology used therewith. (See also PCT application 92-01815 also incorporated by reference.)

The use of such a microprocessor with a drug delivery device is disclosed in our earlier filed U.S. patent application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the pre-programmed information, is plugged into the device. For each of these three embodiments, changing the programming of the memory device readable by a microprocessor will radically change the behavior of the device by causing the microprocessor to be programmed in a different manner. This is done to accommodate different drugs for different types of treatment.

In a preferred embodiment of the methodology of the invention several different criteria are considered. (1) The inspiratory flow rate and inspiratory volume are simultaneously and separately considered to insure repeatability. (2) The drug is released inside the parameters of FIGS. 7, 8 or 9 with FIG. 9 parameters being most preferred. (3) The particle size of the released drug is in the range of 0.5 to 5 microns and 80% or more and the particles have the same size as the average particle size ±10% in size. (4) The drug particles are released at a velocity which is obtained at a flow rate in the range of greater than −2.0 liters/sec. and less than 2.0 liters/sec. As indicated early the actual velocity can vary based on a number of factors. The release velocity should be determined so that the particles are at or are slowed to zero velocity after traveling about 0.5 to 2 cm from the release point. The speed being measured from the drug release point in a direction toward the back of the throat of the patient.

After dosing a patient with a systemic peptide drug it is desirable to take blood samples and make adjustments as needed to obtain the desired drug to blood ratio. In accordance with all methods the patient does not push a button to release drug. The drug is released automatically by signals from the microprocessor using measurements obtained.

The amount of peptide hormone drug delivered to the patient will vary greatly depending on the particular drug being delivered. In accordance with the present invention it is possible to deliver a wide range of different peptide hormone drugs. The drugs must pass through pulmonary membranes and, as such, are preferably small-less than 50 amino acids, more preferably, less than 27 amino acids, in size. The most preferred drugs include leuprolide and calcitonin. Peptide hormone drugs are generally administered to a patient in an amount in the range of about 10 μg–100 μg. Useful hormones are listed below in Table 1.

TABLE 1

Useful Peptide Hormone Drugs

| Compound | Amino acids |
| --- | --- |
| Somatostatin | 6 |
| Oxytocin | 9 |
| Desmopressin | 9 |
| LHRH | 10 |
| Nafarelin | 10 |
| Leuprolide | 11 |
| ACTH analog | 17 |
| Secretin | 27 |
| Glucagon | 29 |
| Calcitonin | 32 |
| GHRH | 40 |
| Growth hormone | 191 |

These doses are based on the assumption that when intrapulmonary delivery methodology is used the efficiency of the delivery is approximately 10% and adjustments in the amount released must be made in order to take into account the efficiency of the device. The differential between the amount of hormone drug actually released from the device and the amount of hormone drug actually delivered to the patient varies due to a number of factors. As shown in FIGS. 6–9 devices used with the present invention are approximately 20% efficient, however, the efficiency can be as low as 10% and as high as 50% ore more meaning that as little as 10% of the released peptide hormone drug may actually reach the circulatory system of the patient and as much as 50% or more might be delivered. The efficiency of the delivery will vary somewhat from patient to patient and must be taken into account when programming the device for the release of peptide hormone drug. In general, a conventional metered dose inhaling device is about 10% efficient.

When administering hormone drug using an inhalation device of the present invention, the entire dosing event can involve the administration of anywhere from 1 μg to 100 mg, but more preferably involves the administration of approximately 10 μg to 10 mg of peptide drug. The large variation in the amounts which might be delivered are due to the fact that different drugs have greatly different potencies and may be delivered from devices which vary greatly in terms of the efficiency of drug delivered. The entire dosing event may involve several inhalations by the patient with each of the inhalations being provided with multiple bursts of peptide hormone drug from the device.

In addition to drug potency and delivery efficiency, peptide hormone drug sensitivity must be taken into consideration. The present invention makes it possible to vary dosing over time if the sensitivity of the patient changes and/or if user compliance and/or lung efficiency changes over time.

Dynamic Particle Size Adjustment

When aerosolized particles are released from a drug delivery device in accordance with the methodology of the invention, the particles can change in size due to evaporation of water from the particles. Further, if the surrounding atmosphere is particularly humid, the particles can increase in size. In order to obtain reproducibility in dosing, it is desirable to create a surrounding environment such that the particles do not increase or decrease in size regardless of the humidity. In order to obtain such, it is possible to incorporate into the device a means for adding energy to the air surrounding the aerosolized particles. By doing such, it is possible to minimize the effect of water vapor which might be present within the air and to obtain a predetermined amount of evaporation of water from the particles. It is also possible to add water vapor so as to saturate the atmosphere surrounding the particles and thereby prevent the particles from undergoing evaporation. The correct technique to be used depends on the particular drug and the particular situation which the device is being used within. Various means for effecting the size of particles are disclosed within U.S. patent application Ser. No. 08/313,461 filed Sep. 27, 1994, which application is incorporated herein in its entirety and specifically incorporated in order to disclose means for dynamically effecting the size of aerosolized particles.

Dosing Methodology

Based on the above, it will be understood that the dosing or amount of drug actually released from the device can be changed based on the most immediately prior monitoring event wherein the inspiratory flow of a patient's inhalation is measured.

The dosing program can be designed with some flexibility. For example, if the patient normally requires 25 mg per day of drug, the microprocessor of the inhalation device can be programmed to prevent further release of the valve after 35 mg have been administered within a given day. Setting a slightly higher limit would allow for the patient to administer additional hormone drug, if needed, due to misdelivery of hormone drug such as due to coughing or sneezing during an attempted delivery.

The ability to prevent overdosing is a characteristic of the device due to the ability of the device to monitor the amount of peptide hormone drug released and calculate the approximate amount of peptide hormone drug delivered to the patient based on monitoring given events. The ability of the present device to prevent overdosing is not merely a monitoring system which prevents further manual actuation of a button. As indicated above, the device used in connection with the present invention is not manually actuated, but is fired (i.e., drug released) in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of peptide hormone drug merely by the manual actuation of a button to fire a burst of hormone drug into the air or a container.

The microprocessor will also include a timing device. The timing device can be electrically connected with visual display signals as well as audio alarm signals. Using the timing device, the microprocessor can be programmed so as to allow for a visual or audio signal to be sent when the patient would be normally expected to administer peptide drug. In addition to indicating the time of administration (preferably by audio signal), the device can indicate the amount of peptide drug which should be administered by providing a visual display. For example, the audio alarm could sound alerting the patient that hormone drug should be administered. At the same time, the visual display could indicate "50 µg" as the amount of peptide drug to be administered. At this point, a monitoring event could take place. After completion of the monitoring event, administration would proceed and the visual display would continually indicate the remaining amount of peptide drug which should be administered. After the predetermined dose of 50 µg had been administered, the visual display would indicate that the dosing event had ended. If the patient did not complete the dosing event by administering the stated amount of peptide drug, the patient would be reminded of such by the initiation of another audio signal, followed by a visual display instructing the patient to continue administration.

Additional information regarding dosing with peptide drug via injection can be found within Wearley, L. L., "Recent Progress in Protein and Peptide Delivery by Noninvasive Router," *Critical Reviews in Therapeutic Drug Carrier Systems,* 8(4):331–394 (1991) and Harrison's—*Principles of Internal Medicine* (most recent edition) published by McGraw Hill Book Company, New York, incorporated herein by reference to disclose information regarding the dosing of hormone drugs.

Delivery Device

Figure 10:
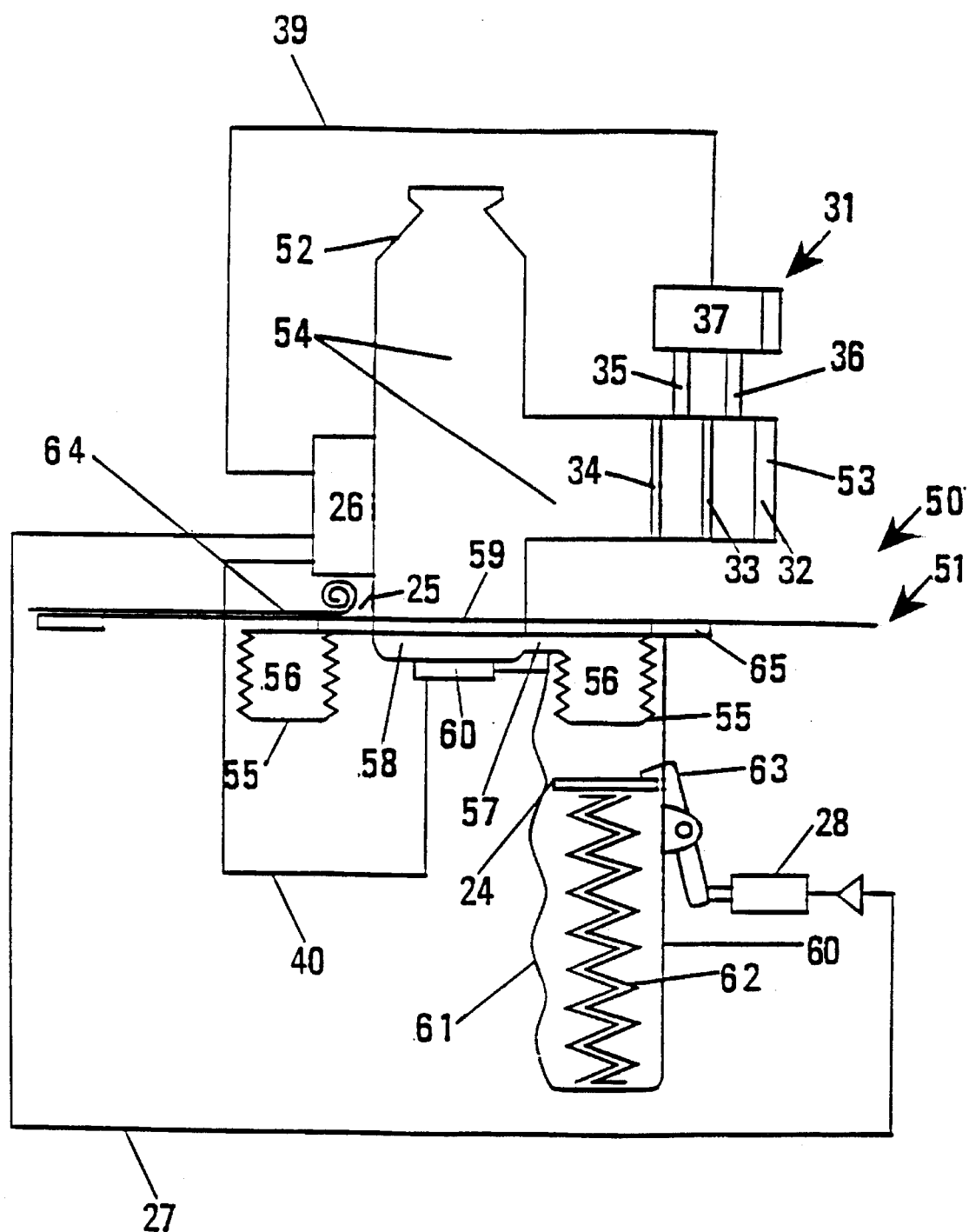

There are two preferred types of devices which can be used with the present invention. In general, one type uses a low boiling point propellant and the other uses aqueous formulations. The devices which use low boiling point propellants are shown in FIGS. 1–4 and an embodiment of a device which uses aqueous formulations is shown in FIG. 10. Regardless of which type is used the device is a hand-held, portable device which is comprised of (a) a means for separately measuring and analyzing the inspiratory flow rate and inspiratory volume of a patient and (b) a means for automatically releasing a measured amount of a peptide drug into the inspiratory flow path of a patient, e.g. an automatic valve actuation means or mechanism for moving formulation through a porous membrane. In order to use the device, the device must be "loaded", i.e. connected to (c) a source of peptide drug which, in general, is formulated in water or in a low boiling point propellant. The entire device is light weight (less than 1 kg loaded) and portable.

A formulation of a peptide drug in a low boiling point propellant is typically contained in a pressurized canister which is connectable to the "unloaded" device, i.e., the device without the container. When the container of propellant and peptide drug is connected to the device, the container will include a valve opening at one end which opening is seated into a flow path within the device. The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it releases a valve allowing drug and propellant to escape into the inspiratory flow path of the device and ultimately into the patient's lungs. After being released, the drug and propellant will preferably pass through a nozzle prior to entering the inspiratory flow path of the device and thereafter the lungs of the patient.

It is important to note that the firing threshold of the device is not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug. The high degree of dosing repeatability needed to deliver peptide drugs may be obtained merely by measuring and releasing at the same measured flow rate and volume for each release of drug. Further, the device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time.

FIG. 1 shows a cross-sectional view of a hand-held, portable, electronic breath-actuated inhaler device which can be used in connection with the present invention. The device is shown with a holder 1 having cylindrical side walls and a removable cap. The holder 1 is "loaded" in that it includes the pressurized canister 3. The canister 3 includes a non-metering valve 5 which is held down in the open position when the cap 2 is screwed down, thus setting the valve 5 into a seat 6 which is in connection with a flow path 8.

A formulation 4 comprised of a peptide drug such as leuprolide or calcitonin and a suitable propellant, such as a low boiling point propellant, is contained within the pressurized canister 3. Propellant and peptide drug are released from the canister 3 via the electrically controlled solenoid 7. In that the valve 5 of the canister is continuously open, another valve, contained within solenoid 7, facilitates the release of the drug. When the solenoid 7 allows release of propellant and drug, the propellant and drug flows through the flow path 8 and then through the solenoid actuated valve 9 into the flow path 10, out through the nozzle 13 and then into the inspiratory flow path 11 surrounded by walls 12.

It is important to note that a variety of devices can be used in order to carry out the endocrine therapy delivery methodology of the present invention. However, the device must be capable of allowing the release of a metered amount of peptide drug based on pre-programmed criteria relating to flow rate and volume. These measurements may be made mechanically but are preferable electronic and are readable by the microprocessor 22. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 22, containing read only memory which in turn contains the pre-programmed information, is plugged into the device. For each of these three embodiments, changing the programming of the memory device readable by microprocessor 22 will radically change the behavior of the device by causing microprocessor 22 to be programmed in a different manner. As regards the present invention, the non-volatile memory contains information relevant only to the administration of a specific peptide drug such as recombinately produced growth hormone. Microprocessor 22 sends signals to solenoid 7 which determines the amount of drug delivered into the inspiratory flow path. Further, microprocessor 22 keeps a record of all drug dosing times and amounts using a read/write non-volatile memory which is in turn readable by an external device. The formulation 4 contained within canister 3 is released into the atmosphere ultimately via nozzle 13 which opens into inspiratory flow path 11. It is at this point that the low boiling point propellant within formulation 4 flashes, i.e. rapidly evaporates, thus providing particles of peptide drug in an aerosol which is introduced into the mouth and then into the lungs of the patient. In order to allow for ease of use, it is possible to form inspiratory flow path 11 into a mouth piece which can be specifically designed to fit the mouth of a particular patient using the device.

The solenoid 7, and associated valve 9, flow paths 8 and 10, as well as nozzle 13 make up the aerosol delivery system 14 shown by the dotted lines within FIG. 1. The system 14 is in connection with the flow sensor 15 which is capable of measuring a flow rate of about 0 to about 300 liters per minute. The flow sensor 15 includes screens 16, 17 and 18 which are positioned approximately ¼" apart from each other. Tubes 19 and 20 open to the area between the screens 16, 17 and 18 with the tubes 19 and 20 being connected to a conventional differential pressure transducer 21. When the user draws air through inspiratory flow path 11, air is passed through the screens 16, 17 and 18 and the air flow can be measured by the differential air pressure transducer 21. The flow sensor 15 is in connection with the aerosol delivery system 14, and when a threshold value of air flow is reached, the aerosol delivery system 14 allows the release of formulation 4 so that a controlled amount of peptide drug is delivered to the patient. Solenoid 7 is connected to a microprocessor 22 via an electrical connection. The details of the microprocessor and the details of other drug delivery devices which might be used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose devices as shown within FIG. 1 and the microprocessor and program technology used therewith.

Figure 2:
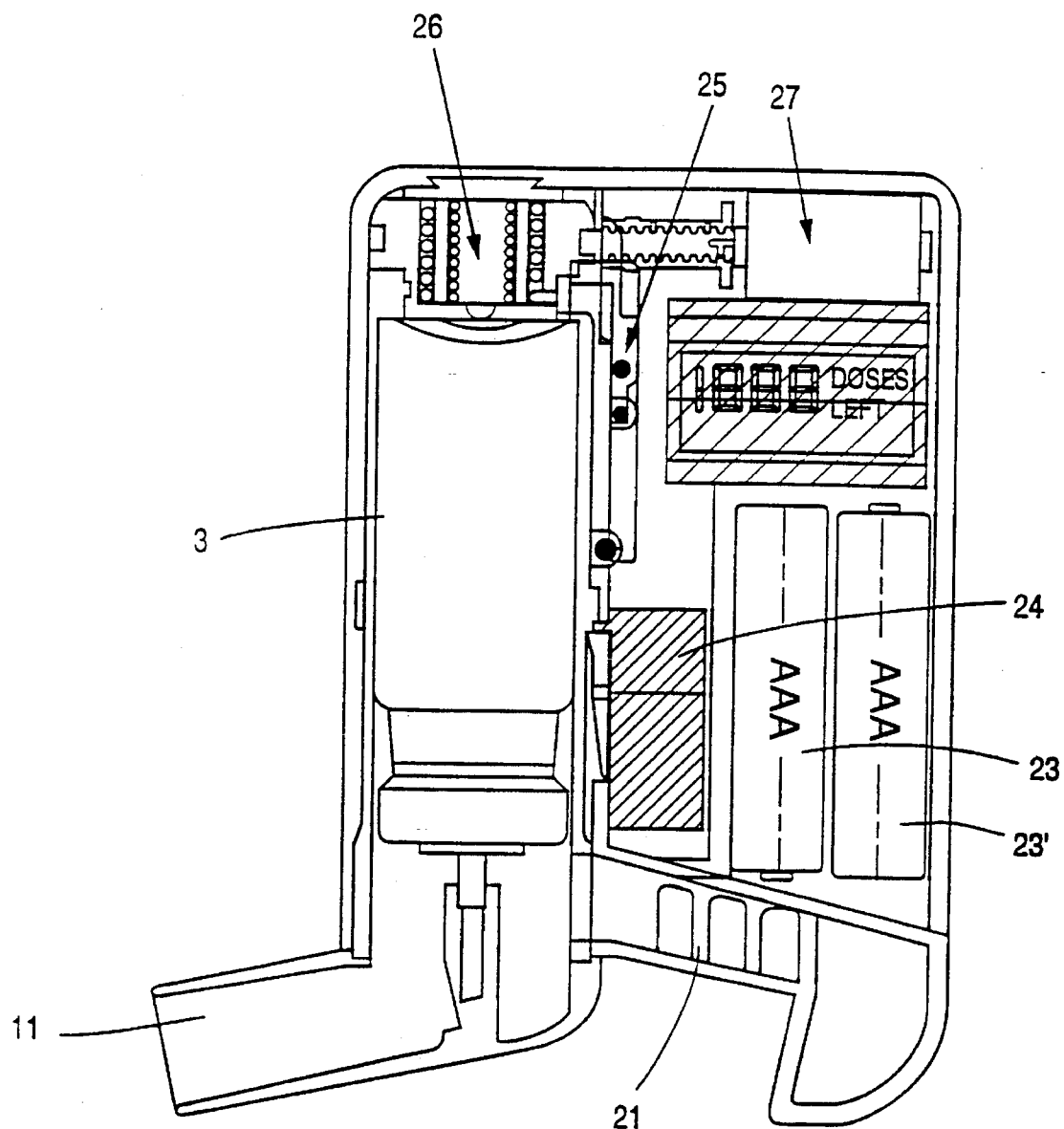

A cross-sectional view of yet another (and more preferred) embodiment of the hand-held, electronic, breath-actuated inhaler device of the invention is shown in FIG. 2. The device of FIG. 2 shows all of the components present within the single hand-held, portable device, i.e. the power source not shown in FIG. 1 is shown in the device in FIG. 2. Like the device shown within FIG. 1, the device of FIG. 2 includes a canister 3 which includes a canister valve 5. However, unlike the device of FIG. 1, the device of FIG. 2 does not have the valve continuously open but allows a valve 5 connected to the canister 3 to be opened by the mechanical force generated by a valve actuation mechanism 26 which is a motor driven, mechanical mechanism powered by a power source such as batteries 23 and 23'. However, like the device shown within FIG. 1, the patient inhales through inspiratory flow path 11 which can form a mouth piece in order to obtain a metering event using the differential pressure transducer 21. Further, when the inspiratory flow meets a threshold of a pre-programmed criteria, the microprocessor 24 sends a signal to an actuator release mechanism 25 which actuates the actuation mechanism 26 forcing canister 3 downward so that canister valve 5 releases formulation into the inspiratory flow path 11. Further details regarding the device of FIG. 2 are described within co-pending U.S. patent application entitled "An Automatic Aerosol Medication Delivery System and Methods", filed on Jan. 29, 1993 as Ser. No. 08/002,507, which application is incorporated herein by reference in its entirety and specifically incorporated in order to describe and disclose devices as shown within FIG. 2 and the microprocessor and program technology used therewith.

Microprocessor 24 of FIG. 2 includes an external non-volatile read/write memory subsystem, peripheral devices to support this memory system, reset circuit, a clock oscillator, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of peptide drug to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason, e.g. abdominal incisional pain resulting in low tidal volumes. Determination of optimal drug delivery points in the inspiratory flow can be done at each dosing event, daily, weekly, or with the replacement of a new canister in the device.

The microprocessor of the present invention, along with its associated peripheral devices, can be programmed so as to prevent the release of drug from the canister from occurring more than a given number of times within a given period of time. This feature makes it possible to prevent overdosing the patient. The overdose prevention feature can be particularly designed with each individual patient in mind or designed with particular groups of patients in mind.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. The devices of FIGS. 1 and 2 have been put forth in connection with devices which use a low boiling point propellant and preferably use that propellant in combination with a suspension formulation which includes the dry powdered peptide drug within the low-boiling-point propellant. Those skilled in the art will readily recognize that such devices can be used for administering a solution of drug within the low-boiling-point propellant. However, those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

Aqueous System Device

The device of FIGS. 1 and 2 can be used to deliver a formulation of peptide drug and low boiling point propellant. The system shown in FIG. 10 is used to deliver a formulation of peptide drug in a carrier of water and/or ethanol. An embodiment of such a device will now be described in detail.

The device 50 shown in FIG. 10 is loaded with a disposable package 51. To use the device 50 a patient (not shown) inhales air from the mouthpiece 52. The air drawn in through the opening 53 and flows through the flow path 54. The package 51 is comprised of a plurality of containers 55. Each container 55 includes a drug formulation 56 and is in fluid connection via a channel 57 with the cavity 58. The cavity 58 is covered by the porous membrane 59. A vibration device 60 may be positioned directly below the cavity 58.

The device 50 is a hand-held, portable device which is comprised of (a) a device for holding a disposable package with at least one but preferably a number of drug containers, (b) a mechanical mechanism (e.g. piston or vibrator for moving the contents of a container (on the package) through a porous membrane (c) a device for measuring the inspiratory flow rate and separately determining the inspiratory volume of a patient, and (d) a switch for automatically releasing or firing the mechanical means after the inspiratory flow rate and/or volume reaches a predetermined point. If the device is electronic it also includes (e) a source of power.

The device for holding the disposable package may be nothing more than a narrow opening created between two outwardly extending bars or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to roller(s) so that when they are rotated, they move the package from one container to the next. A power source driving the roller(s) can be programmed to rotate the rollers only enough to move the package from one container to the next. In order to use the device, the device must be "loaded," i.e. connected to a package which includes drug dosage units having liquid, flowable formulations of pharmaceutically active drug therein. The entire device is self-contained, light weight (less than 1 kg preferably less than 0.5 kg loaded) and portable.

FIG. 10 shows a cross-sectional view of a hand held, self-contained, portable, breath-actuated inhaler device 50 which can be used in the method of the present invention. The device 50 is shown with a holder 60 having cylindrical side walls and a hand grip 61. The holder 2 is "loaded" in that it includes a package 51. The package 51 includes a plurality of containers 56 connected by a connecting member 65.

The embodiment shown in FIG. 10 is a simple version of a device 50 which may be manually actuated and loaded. More specifically, the spring 62 may be compressed by the user until it is forced down below the actuation mechanism 63. When the user pushes the actuation mechanism 63 the spring 62 is released and the mechanical means in the form of a plate 24 is forced upward against a container 56. When the container 56 is compressed its contents are forced out through the channel 57 and membrane 59 and aerosolized. Another container 56 shown to the left is unused. A top cover sheet 64 has been peeled away from the top of the membrane 59 by a peeling means 25. The embodiment of FIG. 10 could provide the same results as a conventional metered dose inhaler. However, the device of FIG. 10 would not require the use of low boiling point propellants such as low boiling point fluorocarbons. Numerous additional features and advantages of the present invention can be obtained by utilizing the monitoring and electronic components described below.

The device must be capable of aerosolizing drug formulation in a container and preferably does such based on pre-programmed criteria which are readable by the microprocessor 26. The details of the microprocessor 26 and the details of other drug delivery devices which include a microprocessor and pressure transducer of the type used in connection with the present invention are described and disclosed within U.S. patent application Ser. No. 07/664,758 filed on Mar. 5, 1991 entitled "Delivery of Aerosol Medications for Inspiration" which application is incorporated in its entirety herein by reference, and is specifically incorporated in order to describe and disclose the microprocessor and program technology used therewith. The use of such a microprocessor with a drug delivery device is disclosed in our earlier filed U.S. patent application Ser. No. 08/065,660 filed May 21, 1993 incorporated herein by reference. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different peptide drugs.

Microprocessor 26 sends signals via electrical connection 27 to electrical actuation device 28 which actuates the means 63 which fires the mechanical plate 24 forcing drug formulation in a container 56 to be aerosolized so that an amount of aerosolized drug is delivered into the inspiratory flow path 54. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 51. The recorded information can be read later by the care-giver to determine the effectiveness of the treatment. In order to allow for ease of use, it is possible to surround the inspiratory flow path 54 with a mouth piece 52.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. The flow sensor 31 includes screens 32, 33 and 34 which are positioned approximately ¼" apart from each other.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 54, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 63 releasing the plate 24 which forces the release of formulation from a container 56 so that a controlled amount of drug is delivered to the patient. The microprocessor 26 is also connected via connector 40 to an optionally present vibrating device 60 which may be activated.

Vibration Device

The ultrasonic vibrations are preferably at right angles to the plane of the membrane 14 and can be obtained by the use of a piezoelectric ceramic crystal or other suitable vibration device 60. The vibrating device 60 in the form of a piezoelectric crystal may be connected to the porous membrane 59 by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 59 allowing for maximum use of the energy towards aerosolizing the liquid formulation 56. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 800 kilohertz (Khz) to about 4,000 kilohertz. The power output required depends upon the amount of liquid being nebulized per unit of time and the area and porosity of the polycarbonate membrane used for producing the drug dosage unit and/or the efficiency of the connection.

Vibration is applied while the formulation 56 is being forced from the pores of the polycarbonate membrane 59. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about one to 200 psi, preferably 50 to 125 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores. In general, the present invention does not create effective aerosols if the viscosity of the liquid is greater than about 50 centipoises.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air or any other gas is forced through openings as the aerosol is forced out of the porous membrane. Accordingly, an air flow is created toward the patient and away from the nozzle opening which carries the formed particles along and aids in preventing their collision with each other. The amount of gas forced from the openings will vary depending upon the amount of aerosol being formed. However, the amount of gas is generally five to two hundred times the volume of the liquid formulation within the container. Further, the flow velocity of the gas is generally about equal to the flow velocity of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced form the container. When a circular opening is used, particles which are towards the center of the circle may not be carried along by the air being forced from the openings and will collide with each other. The elongate rectangle could be formed in a circle, thereby providing an annular opening and air could be forced outward from the outer and inner edges of the circle formed. Further details regarding such are described in U.S. patent application Ser. No. 08/247,012 filed May 20, 1994 which is incorporated herein by reference to disclose and describe such.

Security Features

In that many peptide drugs can be toxic it is desirable to design devices and methodology so as to hinder access to unauthorized users such as children to the extent possible. The methodology and devices of the present invention do so in an number of specific ways.

The device shown within FIG. 2 is designed to be reusable. More specifically, the drug delivery device can be "loaded" with a cassette of the type shown within either of FIGS. 3 and 4. The cassette is comprised of an outer cover 30, a canister 3 and top nozzle piece 31. The components are shown in a disassembled state in FIG. 3. A different embodiment of such components are shown in an assembled state within FIG. 4.

In essence, the cassette shown in FIG. 3 is somewhat less secure than the cassette shown within FIG. 4. As indicated, the top portion of the cover 30 is open within FIG. 3. This allows one to force the canister 3 downward and open the valve 5 to allow release of drug. However, in the embodiment shown in FIG. 4, there is no general opening but only two small openings 34 and 34'. Using the embodiment shown in FIG. 3, the cassette is loaded within the device shown in FIG. 2 and a motor driven piston forces the bottom of the canister 3 downward actuating the valve 5 to an open position. In accordance with the embodiment shown within FIG. 4, a two-pronged fork device is positioned over the end portion of the cover 30'. Each prong of the fork protrudes through an opening 34 and 34' allowing the canister 3 to be forced downward so that the valve 5 can be opened. It should be pointed out that when the cover 30 is attached to the top nozzle piece 31, they can be sealed together using a fastacting glue or any appropriate means making it impossible to separate the components.

In that the peptide drug is contained within the canister 3 with a low boiling point propellant it is extremely difficult to open the canister without losing all of the contents. Accordingly, the contents of the canister can generally be obtained only by including the canister within components 30 and 31 and attaching such to the device shown within FIG. 2.

Figures 3, 4:
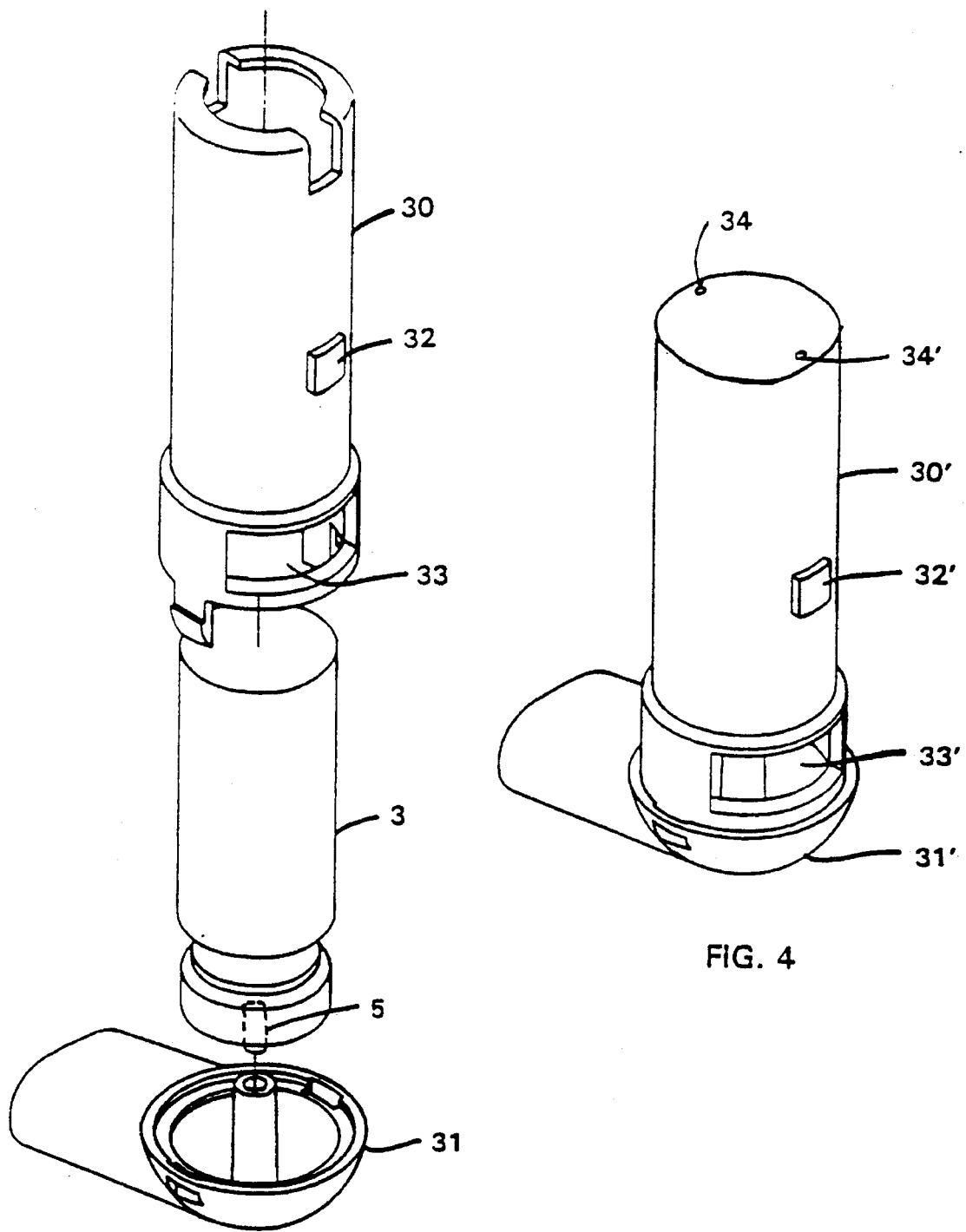

The following description is provided with respect to FIG. 3 and the component shown therein, but is equally applicable with respect to FIG. 4 and the component shown therein. The cover 30 can have protuberances such as the protuberance 32 and openings such as the opening 33 thereon. These openings and protuberances can serve as a type of lock and key mechanism which is interactable with receiving protuberances and openings in the device shown in FIG. 2. Accordingly, unless the cover 30 includes the correct openings and protuberances in the correct position the cover will not fit into the device shown in FIG. 2 and cannot be operated. The body of the device as shown within FIG. 2 is designed so as to be capable of receiving the openings and protuberances on the cover 30. Although devices such as those shown within FIG. 2 might be utilized to dispense a variety of different types of drugs the physical configuration of the device is specific with respect to certain drugs and is particularly specific with respect to peptide drugs. Thus, the cover 30 and receiving body portion on the device of FIG. 2 are designed so that they can be integrated but are also designed so that they will not integrate with other devices not specific for the delivery of peptide drugs. Thus, as a first layer of security the device and methodology of the present invention provides for a physical lock and key interaction.

As a second line of defense against misuse of drugs, it is possible to design the components 31 and 32 and/or the device shown in FIG. 2 so as to receive a signal from a remote transmitter which is worn by the patient for which the drug was prescribed by the prescribing physician. By designing the device in this manner no drug can be released from the device unless the device is in close proximity to the intended user of the device.

It will, of course, be apparent to those skilled in the art that a combination of all or any of the above security features can be used. Further, the transmitting and receiving signals can be by any means of signalling and need not be limited to radio signals and thus could include infrared and other types of signals. Further, other interlocking mechanisms with more complex physical shapes could be readily devised in order to enhance the security of the device.

Nasal Delivery

In place of the mouthpiece referred to above, it is possible to design the flow path 11 so as to include one or two smaller tubes which can fit within the nostrils or a "nose mask"—like covering which encompasses the nostril openings. By designing the end of the flow path 11 in this manner, it is possible to provide for nasal delivery. Using this technique, the peptide drug is delivered by transmucosal permeation and is not generally inhaled into the lungs. Requiring a minimal nasal inspiratory flow prior to firing ensures that nasal congestion is not present which congestion might be exacerbated by drug delivery. Other features of the invention remain the same. In particular, the day and time of day of each monitoring and dosing event is recorded within the device and the patient is signalled regarding the time and the amount of drug to be delivered at each dosing event which information is also recorded. However, in accordance with such a methodology, it is important to take into consideration the differences in efficiency between intrapulmonary and nasal delivery. Dosing adjustments can be made by those skilled in the art by delivering small doses at first and continually increasing the dosage amount while continuing to monitor blood levels of the delivered hormone drug in order to determine what dosing amounts deliver the required amount of peptide drug to carry out appropriate endocrine therapy. Information regarding the bioavailability of certain peptide drugs by nasal delivery is provided below in Table 2.

TABLE 2

Intranasal Bioavailabilities of Proteins and Peptides

| Compound | Amino acids | Bioavailability (%) |
| --- | --- | --- |
| Somatostatin | 6 | 75 |
| Oxytocin | 9 | 1 |
| Desmopressin | 9 | 10 |
| LHRH | 10 | 1.5 |
| Nafarelin | 10 | 2 |
| Leuprolide | 11 | <10 |
| ACTH analog | 17 | 12 |
| Secretin | 27 | 10 |
| Glucagon | 29 | <1 |
| Calcitonin | 32 | <1 |
| GHRH | 40 | <1 |
| Growth hormone | 191 | <1 |

Insulin Containing Package

A package 51 which includes containers 56 is shown within the FIG. 10. This type of package includes the peptide drug formulation in a flowable form within the container 56. However, in another embodiment the peptide component of the formulation is maintained in a dry state substantially free of water in one container while the liquid component of the formulation such as the water is maintained in a separate container. Such a package is shown in figure 11.

Figure 11:
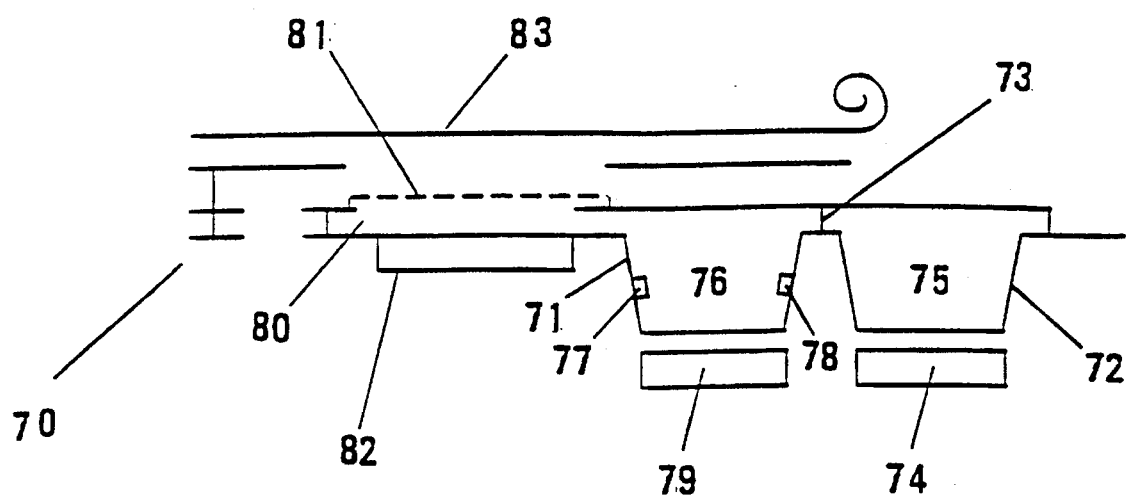

The package 70 of FIG. 11 includes a first container and a second container 72. The containers 71 and 72 are in fluid connection with each other but the fluid connection is interrupted by a membrane 73 which membrane can be ruptured by the application of pressure in an amount of about 50 psi or less. A device such as the component 74 forces against the bottom of the container 72 and forces the contents 75 (which is liquid) against the membrane 73 which is then ruptured. The liquid 75 then enters the container 71 and mixes with the dry powder 76 present with the container 71. The container 71 may include mixing components 77 and 78. These components may be vibrating devices, ultrasonic devices or other suitable mechanisms allowing for the mixing of the liquid with the dry peptide. When the mixing is completed the component 79 is forced against the container 71 forcing the peptide drug formulation present therein into the chamber 80. Once the formulation is in the chamber 80 it is there under pressure and can be moved through the membrane 81 by the application of that pressure and/or by the use of a vibrating device 82. The formulation is moved through the membrane 81 only after removal of the cover sheet 83.

Package structures of the type shown within FIG. 11 are described within U.S. patent application Ser. No. 08/247,012 filed May 20, 1994 which application is incorporated herein by reference to disclose and describe such packages. The membrane 81 includes pores having a diameter in the range of about 0.25 micron to about 6 microns and a pore density in the range of $1 \times 10^4$ to about $1 \times 10^8$ pores per square centimeter. The porous membrane 81 is preferably comprised of a material having a density in the range of about 0.25 to 3.0 mg/cm$^2$, more preferably about 1.7 mg/cm$^2$ and a thickness of about 2 to about 20 microns, more preferably 8 to 12 microns. The liquid 75 present in the container 72 is preferably capable of dissolving the peptide component 76. The peptide powder 76 is preferably completely dissolved within the container 71 prior to being forced into the chamber 80. Dissolving the peptide makes it easier to move the peptide through the pores of the membrane 81 and create a fine mist aerosol. Keeping the dried peptide powder apart from the liquid makes it possible to maintain a longer shelf life.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

We claim:

1. A method of administering a peptide drug for inhalation by a patient, comprising:
   (a) providing a hand-held, self contained device;
   (b) determining a drug release point based upon real time values of both a patient's inspiratory rate and inspiratory volume;
   (c) providing a disposable container having a formulation therein comprising a carrier and peptide drug;
   (d) providing an open channel which includes an abutment therein and placing said open channel in fluid communication with said disposable container;
   (e) providing a porous membrane having pores with a diameter of 0.25 to 6 microns in fluid communication with said open channel;
   (f) moving said formulation from said disposable container through said abutment and into said open channel, the abutment being broken upon application of force thereon by said formulation;
   (g) aerosolizing said formulation by moving said formulation through said open channel and through said porous membrane;
   (h) providing said aerosolized formulation for inhalation by a patient;
   (i) repeating steps (a–h) at substantially the same inspiratory flow rate and inspiratory flow volume and providing a new disposable porous membrane for each aerosolizing step (g).

2. The method of claim 1, wherein the moving (f) occurs at an inspiratory volume in the range of about 0.10 to about 2.0 liters/second and an inspiratory volume in the range of about 0.15 to about 0.80 liters.

3. The method of claim 1, further comprising:
   sending an audible signal to the patient at a predetermined time so as to prompt the patient to administer drug.

4. The method of claim 3, wherein the repeating of (i) is continuously carried out so as to maintain a desired drug to blood ratio in the patient for the appropriate time to allow for endocrine therapy of the patient.

5. The method of claim 1, wherein the moving (f) is automatically carried out by sending an electronic signal to an actuation means which forces formulation into the open channel of the disposable container in response to a received electronic signal.

6. The method of claim 2, wherein the repeating of (i) is carried out over a period of time so as to maintain a desired drug to blood ratio in the patient.

7. The method of claim 1, wherein the peptide drug is leuprolide.

8. The method of claim 1, wherein the peptide drug is calcitonin.

9. The method of claim 1, wherein the peptide drug is a hormone selected from the group consisting of somatostatin, oxytocin, desmopressin, LHRH, nafarelin ACTH analog, secretin glucagon, calcitonin, GHRH, leuprolide, interfereon-β and growth hormone.

10. The method as claimed of claim 1, wherein the peptide drug is administered in an amount in the range of from about 1 μg to about 100 mg.

11. The method as claimed in claim 10, wherein the peptide drug is somatostatin.

12. The method as claimed in claim 10, wherein the peptide drug is selected from the group consisting of oxytocin, desmopressin and nafarelin.

13. The method as claimed in claim 1, wherein the amount of peptide drug administered and time of administration is continually recorded and adjustments are made in the amount of drug administered based on the effect of drug administration on the level of peptide drug in the patient's blood.

14. The method as claimed in claim 13, further comprising:
   retreiving the recorded information regarding the time and amount of peptide drug administered.

15. The method of claim 14, further comprising:
   analyzing the retrieved information to determine desired dosing levels for further administration of peptide drug to the patient.

16. The method as claimed in claim 1, wherein the peptide drug is administered in an amount in the range of from about 1 μg to about 4 mg.

17. The method of claim 1, wherein the releasing occurs at an inspiratory flow rate in the range of about 0.2 to about 1.8 liters per second and an inspiratory volume in the range of about 0.15 to about 0.4 liters.

18. The method of claim 17, wherein the moving occurs at an inspiratory flow rate in the range of about 0.15 to about 1.8 liters per second and an inspiratory volume of about 0.15 to about 0.25 liters.

19. A method of respiratory therapy comprising:
   (a) measuring a patient's respiratory flow rate and inspiratory flow volume;
   (b) providing a disposable container having a peptide hormone formulation therein;
   (c) providing an open channel in fluid communication with said disposable container, providing an abutment in the channel and providing a porous membrane having pores of 0.25 to 6.0 microns in diameter in fluid communication with said open channel;
   (d) forcing said peptide hormone formulation through said abutment, the abutment being broken upon application of force by said peptide hormone formulation thereon;
   (e) aerosolizing said peptide hormone formulation by moving said peptide hormone formulation through said porous membrane;

(f) providing said aerosolized peptide hormone formulation to a patient for inhalation at a predetermined combination of inspiratory flow rate and inspiratory flow volume;

(g) repeating steps (a–f) at substantially the same predetermined combination of inspiratory flow rate and inspiratory flow volume and providing a new disposable porous membrane for each aerosolizing step (e).

20. The method of claim 19, wherein the moving occurs at an inspiratory flow rate in the range of about 0.1 to about 2.0 liters/second and at an inspiratory volume in the range of about 0.15 to about 0.80 liters.

21. The method of claim 20, wherein the drug is administered to the patient at substantially the same time each day.

22. The method of claim 19, further comprising recording the time, date and amount of drug released from a hane-held, self contained device.

23. The method of claim 19, wherein the moving occurs at an inspiratory flow rate in the range of about 0.2 to about 1.8 liters per second and at an inspiratory volume in the range of about 0.15 to about 0.4 liters.

24. The method of claim 23, wherein the moving occurs at an inspiratory flow rate in the range of about 0.15 to about 1.8 liters per second and an inspiratory volume of about 0.15 to about 0.25 liters.

25. A method of administering a peptide drug, comprising:

(a) providing a liquid carrier in a first container;

(b) providing a dry peptide drug in a second container;

(c) providing an open channel which is in fluid communication with each of said first and second containers, providing an abutment within said channel between said first and second containers and providing a porous membrane in fluid communication with said second container;

(d) forcing the liquid carrier from said first container through said abutment and into said second container, the abutment being broken on application of force by said liquid carrier thereupon;

(e) mixing the liquid carrier with the dry peptide drug;

(f) moving the mixed liquid carrier and peptide drug through said porous membrane thereby creating an aerosol;

(g) providing the aerosol for inhalation into the lungs of a patient; and (h) repeating steps (a–g) using a new porous membrane with each moving step (f) and using new first and second containers with each forcing step (d).

26. The method of claim 1, wherein the porous membrane has pores having a diameter in range of from about 0.25 to 6.0 microns thereby creating an aerosol having particles with a diameter in the range of from about 0.5 to 12.0 microns.

27. The method of claim 1, wherein the dry peptide drug is a hormone selected from the group consisting of somatostatin, oxytocin, desmopressin, LHRH, nafarelin ACTH analog, secretin glucagon, calcitonin, GHRH, leuprolide, interferon-$\beta$ and growth hormone.

28. The method of claim 1, wherein the administering is carried out using a hand-held, self-contained device.

29. The method of claim 28, further comprising recording the time, date and amount of drug released from the hand-held, self-contained device.

30. The method of claim 1, wherein the moving occurs at an inspiratory flow rate in the range of about 0.2 to about 1.8 liters per second and an inspiratory volume in the range of about 0.15 to about 0.4 liters.

31. The method of claim 30, wherein the moving occurs at an inspiratory flow rate in the range of about 0.15 to about 1.8 liters per second and an inspiratory volume of about 0.15 to about 0.25 liters.

\* \* \* \* \*